United States Patent [19]

Farrar et al.

[11] Patent Number: 5,760,023
[45] Date of Patent: Jun. 2, 1998

[54] KAPPA AGONIST ANTI-PRURITIC PHARMACEUTICAL FORMULATIONS AND METHOD OF TREATING PRURITUS THEREWITH

[75] Inventors: John J. Farrar, Chester Springs; An-Chih Chang, Bensalem; Virendra Kumar, Paoli; Wei Yuan Zhang, Collegeville; Alan Cowan, Ambler, all of Pa.

[73] Assignee: Adolor Corporation, Malvern, Pa.

[21] Appl. No.: 892,599

[22] Filed: Jul. 14, 1997

[51] Int. Cl.$^6$ .......... A61K 31/16; A61K 31/40; A61K 31/655

[52] U.S. Cl. .......... 514/150; 514/210; 514/255; 514/331; 514/426; 514/613; 514/617; 514/619; 514/620; 514/623

[58] Field of Search .......... 514/150, 210, 514/255, 331, 426, 613, 617, 619, 620, 623

[56] References Cited

U.S. PATENT DOCUMENTS

| | | | |
|---|---|---|---|
| 4,145,435 | 3/1979 | Szmuszkovicz | 424/274 |
| 4,359,476 | 11/1982 | Kaplan et al. | 424/274 |
| 4,360,531 | 11/1982 | McMillan et al. | 424/274 |
| 4,438,130 | 3/1984 | Kaplan | 424/274 |
| 4,663,343 | 5/1987 | Horwell et al. | 514/429 |
| 4,855,316 | 8/1989 | Horwell et al. | 514/422 |
| 4,906,655 | 3/1990 | Horwell et al. | 514/422 |
| 4,929,627 | 5/1990 | Pannev | 514/320 |
| 4,943,578 | 7/1990 | Naylor et al. | 514/252 |
| 5,114,945 | 5/1992 | Hayes et al. | 514/278 |

FOREIGN PATENT DOCUMENTS

| | | |
|---|---|---|
| 0 108 602 | 5/1984 | European Pat. Off. |
| 0 254 545 | 1/1988 | European Pat. Off. |
| 0 260 555 | 3/1988 | European Pat. Off. |
| 0 261 842 | 3/1988 | European Pat. Off. |
| 0 325 406 | 7/1989 | European Pat. Off. |
| 0 330 467 | 8/1989 | European Pat. Off. |
| 0 330 469 | 8/1989 | European Pat. Off. |
| 0 333 427 | 9/1989 | European Pat. Off. |
| 0 356 247 | 2/1990 | European Pat. Off. |
| 0 366 327 | 5/1990 | European Pat. Off. |
| 0 372 466 | 6/1990 | European Pat. Off. |
| 0 393 696 | 10/1990 | European Pat. Off. |
| 0 398 720 | 11/1990 | European Pat. Off. |
| 0 409 489 | 1/1991 | European Pat. Off. |
| 0 483 580 | 10/1991 | European Pat. Off. |
| 0 577 847 | 1/1994 | European Pat. Off. |
| 0 752 246 | 1/1997 | European Pat. Off. |
| WO 90/07502 | 7/1990 | WIPO |
| WO 92/20657 | 11/1992 | WIPO |
| WO 94/18165 | 8/1994 | WIPO |
| WO 96/06077 | 2/1996 | WIPO |
| WO 96/06078 | 2/1996 | WIPO |

OTHER PUBLICATIONS

IL Farmaco, 50(6), 405–418 (1995).
McMahon et al., TINS, vol. 15, No. 12 (1992).
Bernstein et al., Journal of Investigative Dermatology, 78:82–83 (1982).
Ballantyne et al., Pain, 33:149–160 (1988).
J.D. Bernhard, J. Am. Acad. Derm. 24:309 (1991).
IASP Newsletter, Sep./Oct. 1996.
Thomas et al., Brain Research, 695:267–270 (1995).

*Primary Examiner*—Leonard Schenkman
*Attorney, Agent, or Firm*—Imre Balogh

[57] ABSTRACT

Anti-pruritic pharmaceutical formulations containing kappa agonist compounds and methods of prevention or treatment of pruritus in a mammal with the anti-pruritic formulations.

10 Claims, No Drawings

KAPPA AGONIST ANTI-PRURITIC PHARMACEUTICAL FORMULATIONS AND METHOD OF TREATING PRURITUS THEREWITH

BACKGROUND OF THE INVENTION

1. Field of the Invention

This invention relates to pharmaceutical formulations containing kappa agonist compounds and to their medical use as anti-pruritic agonist at kappa opioid receptors.

2. Reported Developments
A) Antihyperalaesic Kappa Agonists

Opium and its derivatives are potent analgesics that also have other pharmacological effects, and exert their effects by interacting with high-affinity receptors.

It has been shown by investigators that there are at least three major opioid receptor types in the central nervous system (hereinafter CNS) and in the periphery. These receptors, known as mu ($\mu$), delta ($\delta$) and kappa ($\kappa$), have distinct pharmacological profiles, anatomical distributions and functions. [See, for example: Wood, P. L., Neuropharmacology, 21, 487–497, 1982; Simon, E. J., Med. Res. Rev., 11, 357–374, 1991; Lutz et al, J. Recept. Res. 12, 267–286; and Mansour et al, Opioid I, ed. Herz, A. (Springer, Berlin) pp. 79–106, 1993.] The $\delta$ receptors are abundant in CNS and mediate analgesia, gastrointestinal motility and various hormonal functions. The $\mu$ receptors bind morphine-like drugs and mediate the opiate phenomena associated with morphine, including analgesia, opiate dependence, cardiovascular and respiratory functions, and several neuroendocrine effects.

The $\kappa$ receptors have a wide distribution in CNS and mediate a spectrum of functions including the modulation of drinking, water balance, food intake, gut motility, temperature control and various endocrine functions. They also produce analgesia. [See, for example: Leander et al, J. Pharmacol. Exp. Ther. 234, 463–469, 1985; Morley et al, Peptides 4, 797–800, 1983; Manzanares et al, Neuroendocrinology 52, 200–205, 1990; and Iyengar et al, J. Pharmacol. Exp. Ther, 238, 429–436, 1986.]

Most clinically used opioid analgesics such as morphine and codeine act as $\mu$ receptor agonists. These opioids have well-known, undesirable and potentially dangerous dependence forming side effects. Compounds which are $\kappa$-receptor agonists act as analgesics through interaction with $\kappa$ opioid receptors. The advantage of these agonists over the classical $\mu$ receptor agonists, such as morphine, lies in their ability to cause analgesia while being devoid of morphine-like behavioral effects and addiction liability.

B) Antihyperalgesic Kappa Agonists as Anti-Pruritic Agents

The prior art has investigated the physiology and treatment of pruritus as illustrated hereunder.

Itch is a well known sensory state associated with the desire to scratch. As with pain, itch can be produced by a variety of chemical, mechanical, thermal or electrical stimuli. In addition to the difference in the sensory quality of itch and pain, they also differ in that (1) itch, unlike pain, can only be evoked from the superficial layers of skin, mucosa, and conjunctiva, and (2) itch and pain usually do not occur simultaneously from the same skin region; in fact, mildly painful stimuli, such as scratching, are effective in eliminating itch. In addition, the application of histamine to skin produces itch but not pain. Itch and pain are further dissociated pharmacologically: itch appears to be insensitive to opiate and non-steroidal anti-inflammatory drug (NSAID) treatment, both of which are effective in treating pain.

Although itch and pain are of a class in that both are modalities of nociception transmitted by small unmyelinated C fibers, evidence that itch is not just a variety of low-threshold pain is overwhelming. Itch leads to the reflex or urge to scratch; pain leads to withdrawal. Removal of the epidermis eliminates itch but causes pain. Analgesics, particularly opiods, relieve pain but often cause itch (see, for example J. Am. Acad. Derm. 24: 309–310, 1991). There can be no doubt that itching is of eminent clinical importance; many systemic and skin diseases are accompanied by persistent or recurrent itch attacks. Current knowledge suggests that itch has several features in common with pain but exhibits intriguing differences as well (see, for example, W. Magerl, IASP Newsletter, pp. 4–7, September/October 1996).

McMahon et al (TINS, Vol. 15, No. 12, pp. 497–501, 1992) provides a description of stimuli (Table a) and a comparison of the established features of itch and pain (Table b):

TABLE a

Stimuli that can elicit or augment itch

Physical

Mechanical. Light touch, pressure, suction.
Thermal. Warming.
Electrical. Focal transcutaneous repetitive stimulation, transcutaneous constant current stimulation, intraneural microstimulation.

Chemical

Non-specific irritants. Acids, alkalis.
Inflammatory mediators. Histamine, kallikrein, bradykinin, prostaglandins.
Histamine-releasing substances. Compound 48/80, protamine, C3a.
Peptidases. Mucunain, papain, trypsin, mast cell chymase.
Neuropeptides. Substance P, vasoactive intestinal polypeptide, neurotensin, secretin.
Opioids. Morphine, $\beta$-endorphin, enkephalin analogues.

TABLE b

Comparison of the established features of itch and pain

| | ITCH | PAIN |
|---|---|---|
| Psychophysiology | | |
| Tissue | Skin. Mucous membranes | Most tissues |
| Stimulus | See Table a | Many stimuli |
| Intraneural microstimulation | Occasionally | Yes |
| Secondary sensations | Allokinesis (itchy skin) | Hyperalgesia |
| Psychogenic modification | Pronounced | Present |
| Counterstimuli | Scratching, pain, cooling | Tactile stimuli, cooling |
| Neurophysiology | | |
| Primary afferent neurones | C- and A$\delta$-fibres | C- and A$\delta$-fibres |
| Flare size | Large | Small |
| Spinal pathway | Anterolateral funiculus | Anterolateral funiculus |
| Protective reflexes | Scratching, sneezing | Flexion, guarding |
| Autonomic reflexes | Yes | Yes |
| Pharmacology | | |
| Capsaicin sensitivity | Yes | Chemogenic pain; yes |
| NSAID sensitivity | Probably not | Yes |
| Morphine sensitivity | No | Yes |

Abbreviation: NSAID, non-steroidal anti-inflammatory drugs.

Experimental focal itch stimuli are surrounded by a halo of seemingly unaffected tissue where light tactile stimuli are capable of eliciting itch-like sensations. The term itchy skin or allokinesis has been coined for these secondary sensations that are reminiscent of the features of secondary hyperalgesia evolving around a painful focus. A crucial observation is that itch and pain usually do not coexist in the same skin region and a mild noxious stimulus such as scratching is in fact the singly most effective way to abolish itch. This abolition of itch can be prolonged producing an 'antipruritic state'. Although mild scratch is often not painful, microneurographic recordings from humans have directly determined that such stimuli are among the most effective ways to excite cutaneous unmyelinated nociceptive afferents. (See, for example:

Shelly, W. B. and Arthur, R. P. (1957) *Arch. Dermatol.* 76, 296–323;

Simone, D. A. et al. (1987) *Somnatosens. Res.* 5, 81–92;

Graham, D. T., Goodell, H. and Wolff, H. G. (1951) *J. Clin. Invest.* 30, 37–49;

Simone, D. A., Alreja, M. and LaMotte, R. H. (1991) *Somatosens, Mot. Res.* 8, 271–279;

Torebjörk, E (1985) *Philos. Trans. R. Soc. London Ser.* B 308, 227–234; and

Vallbo, A. B., Hagbarth, K. E., Torebjörk, H. E. and Wallin, B. G. (1979) *Physiol. Rev.* 59, 919–957).

Physiologically, there is evidence that substance P released from nociceptor terminals can cause the release of histamine from mast cells. Activation of mast cells, with release of the pruritogen histamine, occurs in immediate type hypersensitivity diseases, such as anaphylactic reactions and urticaria. Urticarial eruptions are distinctly pruritic and can involve any portion of the body, and have a variety of causes beyond hypersensitivity, including physical stimuli such as cold, solar radiation, exercise and mechanical irritation. Other causes of pruritus include: chiggers, the larval form of which secretes substance that creates a red papule that itches intensely; secondary hyperparathyroidism associated with chronic renal failure; cutaneous larva migrans, caused by burrowing larvae of animal hookworms; dermal myiasis, caused by maggots of the horse botfly, which can afflict horseback riders; onchocerciasis ("river blindness") caused by filarial nematodes; pediculosis, caused by lice infestations; enterobiasis (pinworm) infestations, which afflict about 40 million Americans, particularly school children; schistosome dermatitis (swimmer's itch); psoriasis; poison ivy; and asteatotic eczema ("winter itch"). The role of histamine or other endogenous pruritogens in mediating itch associated with these and other pruritic conditions, such as atopic dermatitis, its not yet well established. For atopic dermatitis, in particular, it appears that itch is not inhibited by antihistamines, but by cyclosporin A, a drug which inhibits the production of cytokines which have been proposed as potential pruritogens.

Current therapies for the treatment of itch include a variety of topical and systemic agents, such as steroids, antihistamines, and some psychotherapeutic tricyclic compounds, such as doxepin hydrochloride. Many such agents are listed in *PDR Generics* (see Second Edition, 1996, p. cv for a listing of said agents). The limitations of these agents are well known to medical practitioners, and are summarized in the "Warnings" and "Precautions" sections for the individual agents listed in *PDR Generics*. In particular, the lack of complete efficacy of antihistamines is well known, but antihistamines are frequently used in dermatology to treat pruritus due to urticaria, atopic dermatitis, contact dermatitis, psoriasis, and a variety of other conditions. Although sedation has been a frequent side effect of conventional systemically administered antihistamines, a new generation of antihistamines have been developed that are nonsedating, apparently due to their inability to cross the blood-brain barrier.

Intravenous administration of opiate analgesics, such as morphine and hydromorphone has been associated with pruritus, urticaria, other skin rashes, and wheal and flare over the vein being injected. These itch and itch-related reactions are believed to be due to a histamine-releasing property of these opiates, via mast cell degranulation. These opiates are thought to act upon the mu subtype of opiate receptor, but the possibility of interactions at the other principal opiate receptor subtypes (delta and kappa) cannot be excluded since these and other pruritogenic analgesics are not pure mu agonists. The cellular loci of the receptor type(s) mediating the itching effect is not known, although the mast cell is a possible candidate since opiates cause histamine release from these cells. However, some investigators have suggested that the frequent inability of antihistamines to block morphine-induced itching suggests a non-histaminergic mediation of opiate-induced itching—mechanism which could involve central opiate receptors. Although i.v. morphine only occasionally results in generalized itching (in about 1% of patients), pruritus is more prevalent in opiate analgesia with epidural (8.5%) or intraspinal (45.8%) administration. (See, for example: Bernstein et al., "Antipruritic Effect of an Opiate Antagonist, Naloxone Hydrochloride", *The Journal of Investigative Dermatology*, 78:82–83, 1982; and Ballantyne et al., "Itching after epidural and spinal opiates", *Pain*, 33: 149–160, 1988.)

To date, treatment with opiates has not only proven useless in the treatment of itch, but appears to exacerbate itch in mammals. The consistent findings from human studies indicate that whether by central or peripheral mechanisms, opiates appear to promote rather than prevent itching, and that opiate antagonists have antipruritic activity.

Human clinical studies have generally shown that opiates cause itching and there is evidence that these effects can be reproduced in animal models, where itching sensations per se cannot be reported, but scratching behavior can be observed. (See, for example: Thomas et al., "Microinjection of morphine into the rat medullary dorsal horn produces a dose-dependent increase in facial-scratching", *Brain Research*, 695: 267–270, 1996; Thomas et al., "Effects of central administration of opioids on facial scratching in monkeys", *Brain Res.*, 585: 315–317, 1992; and Thomas et al., "The medullary dorsal horn: A site of action of opioids in producing facial scratching in monkeys", *Anesthesiology*, 79: 548–554, 1993).

We have now discovered that certain kappa agonists, which are substantially devoid of central nervous system effects, possess anti-pruritic activity in addition to antihyperalgesic activity. Accordingly, the present invention also provides safe and effective compositions for the prevention and treatment of pruritus.

Compounds having kappa opioid agonist activity are disclosed in the following references all of which are incorporated herein by reference:

1. U.S. Pat. No. 4,145,435
2. U.S. Pat. No. 4,360,531
3. U.S. Pat. No. 4,359,476
4. EPA 0 108 602
5. U.S. Pat. No. 4,855,316
6. EPA 0 393 696
7. EPA 0 372 466
8. U.S. Pat. No. 4,906,655

9. U.S. Pat. No. 4,438,130
10. U.S. Pat. No. 4,663,343
11. U.S. Pat. No. 5,114,945
12. U.S. Pat. No. 4,943,578
13. EPA 0 330 467
14. EPA 0 366 327
15. EPA 0 398 720
16. EPA 0 330 469
17. WO 92/20657
18. EPA 0 409 489 A2
19. EPA 0 333 427
20. WO 90/07502
21. EPA 0 356 247
22. EP0 752 246 A2
23. WO 96/06077
24. EP 0 483 580
25. EPA 0 254 545
26. EPA 0 325 406
27. EPA 0 261 842
28. WO 96/06077
29. WO 94/18165
30. WO 96/06078
31. EPA 0 577 847 A1.
32. U.S. Pat. No. 4,929,627 and
33. EPA 0 260 555

SUMMARY OF THE INVENTION

Compositions containing compounds having kappa opioid agonist activity are provided for preventing or treating pruritus. A compound of formulae I, II, Ia, IIb, III, IV and V, or a pharmaceutically acceptable salt thereof, are used in the compositions.

The compounds of formula I have the following structure:

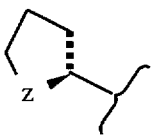

I wherein
the wavy line bond (~) between the nitrogen in the 2-position and the cyclohexyl ring carbon indicates the bond can be either cis- or trans with respect to each substituent on the cyclohexyl ring;

A is a single chemical bond (—), —$(CH_2)_q$, CH($CH_3$)— or —X$(CH_2)_n$
where
q is 1 to 4,
n is 1–4 and
x is O or S;

Ar is an aromatic, hetero-aromatic, bicyclic-aromatic, tricyclic-aromatic group or diphenyl methyl each of which may be unsubstituted or substituted with a member selected from the group consisting of H, halo, trifluoromethyl, nitro, $C_1$–$C_3$-alkoxy, hydroxy, azido, $C_1$–$C_3$-alkyl, methanesulfonyl, cyano, amino, $C_1$–$C_3$-alkoxycarbonyl, $C_1$–$C_3$-alkanoyloxy, and $C_1$–$C_3$-carboxacylamino of the formula —NHC(O)$R_7$
where $R_7$ is H, $C_1$–$C_2$-alkyl, or an aromatic or hetero-aromatic group;

$R_1$ and $R_2$ are independently H, $C_1$–$C_3$-alkyl or allyl;

$R_1$ and $R_2$, taken together with the nitrogen to which they are bonded, complete a ring selected from the group consisting of azetidinyl, pyrrolidinyl, 3-hydroxypyrrolidinyl, 3-fluoropyrrolidinyl, morpholinyl, piperidinyl, and 3,4-dehydropiperidinyl;

$R_3$, $R_4$, $R_5$, $R_6$ are independently H, hydroxy, O$R_8$ or OC(=O)$R_9$;

$R_5$ and $R_6$ taken together may form the group —E—$CH_2$—$CH_2$—E—;

$R_5$ and $R_6$ taken together form a ring

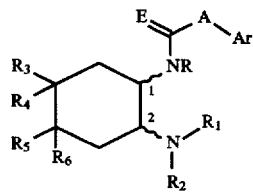

or

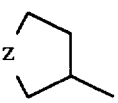

where
Z is selected from the group consisting of oxygen (—O—), N$R_{10}$, sulfur (—S—), sulfinyl (—S(O)—), and sulfonyl (—S(O)$_2$—);

E is N–OH, N–OC(O)$CH_3$, O, S, with the proviso that when E is bivalent sulfur or oxygen, $R_5$ and $R_6$ cannot both be hydrogen;

$R_8$ is $C_1$–$C_3$-alkyl;
$R_9$ is H or $C_1$–$C_3$-alkyl; and
$R_{10}$ is H, or $C_1$–$C_3$-alkyl.

Compounds of the present invention contain one or more asymmetric centers and therefore exist as enantiomers or diastereoisomers. Individual stereoisomers or enantiomers can be obtained from the mixtures by known methods of resolution.

As used herein in formula I:

Ar denotes an aromatic or hetero-aromatic group such as pyridine, thiophene, a bicyclic-aromatic group such as naphthalenes, benzofurans, benzothiophines, a tricyclic-aromatic group such as anthracenes and fluorenes; and halo denotes F, Cl, Br or I.

Preferred compounds within the scope of the invention include the cis- and trans-isomers as well as racemates and enantiomners of the following:

(±)-N-[2-(N,N'-dimethylamino)cyclohexyl]-N-methyl-2-(4-trifluoromethylphenyl)acetamide;

(±)-N-[2-(N',N'-dimethylamino)cyclohexyl]-N-propyl-2-(3-methoxyphenyl)acetamide;

(±)-N-[2-(N',N'-dimethylamino)cyclohexyl]-N-methyl-2-(4-azidophenyl)acetamide;

(±)-N-[2-(N',N'-dimethylamino)cyclohexyl]-N-methyl-2-(3,4-dichlorophenyl)acetamide;

(±)-N-[2-(N',N'-dimethylamino)cyclohexyl]-N-methyl-2-(4-methoxyphenyl)acetamide;

(±)-N-[2-(N',N'dimethylamino)cyclohexyl]-N-methyl-2-(2-naphthyl)acetamide;

(±)-N-[2-(N-cyclopropyl-N-methylamino)cyclohexyl]-2-(4-azidophenyl)acetamide;

(±)-N-(2-(3-acetoxy-1-pyrrolidinyl)cyclohexyl]-N-methyl-2-(3,4-dichlorophenyl)acetamide;

(±)-N-[2-(N-pyrrolidinyl)cyclohexyl]-N-methyl-2-(3,4-dichlorophenyl)acetamide;

(±)-N-[2-(3-hydroxypyrrolidinyl)cyclohexyl]-N-methyl-2-(3,4-dichlorophenyl)acetamide;

(±)-N-[2-[N'-(3-hydroxy-1-azetidinyl]cyclohexyl]methyl-2-(3,4-dichlorophenyl)acetamide;

(±)-N-[2-(N',N'-diethylamino)cyclohexyl]-N-methyl-2-(3,4-dichlorophenyl)acetamide;

(±)-N-[2-(N'-pyrrolidinyl)cyclohexyl]-N-methyl-2-(3,4-dichlorophenyl)propionamide;

(±)-N-[2-(4-methyl-1-piperazinyl)cyclopentyl]-2-(3,4-dichlorophenyl)acetamide;

(±)-N-[2-(N,N-dimethylamino)cyclohexyl]-2-(3,4-dichlorophenyl)acetamide;

(±)-3,4-dichloro-N-methyl-N-[8-(1-pyrrolidinyl)-1,4-dioxaspiro[4.5]dec-7-yl]benzeneacetamide;

(±)-3,4-dichloro-N-methyl-N-[7-(1-pyrrolidinyl)-1,4-dioxaspiro[4.5]dec-8-yl]benzeneacetamide;

(±)-3,4-dichloro-N-methyl-N-[7-(1-pyrrolidinyl)-1,4-dioxaspiro[4.5]dec-6-yl]benzeneacetamide;

(±)-4-bromo-N-methyl-N-[7-(1-pyrrolidinyl)-1,4-dioxaspiro[4.5]dec.8.yl]benzeneacetamide;

(±)-3.fluoro-N-ethyl-N-[7-(1-azetidinyl)-1,4-dioxaspiro[4.5]dec-8-yl]benzeneacetamide;

(±)-3,4-dichloro-N-methyl-N-[7-(1-pyrrolidinyl)-1,4-dioxaspiro[4.4]-non-8-yl)benzeneacetamide;

(±)-3,4-dichloro-N-methyl-N-[7-(1-pyrrolidinyl)-1,4-dioxaspiro[4.6]-undec-8-yl]benzeneacetamide;

(±)-3,4-dichloro-N-methyl-N-[8-(1-pyrrolidinyl)-1,4-dioxaspiro[4.6]-undec-7-yl]benzeneacetamide;

(±)-3,4-dichloro-N-methyl-N-[9-(1-pyrrolidinyl)-1,4-dioxaspiro[4.6]-undec-8-yl]benzeneacetamide;

(±)-3,4-dichloro-N-[4-methoxy-2-(1-pyrrolidinyl)cyclohexyl]-N-methylbenzeneacetamide;

(±)-3,4-dichloro-N-[5-methoxy-2-(1-pyrrolidinyl)cyclohexyl]-N-methylbenzeneacetamide;

(±)-3,4-dichloro-N-methyl-N-[4-oxo-2-(1-pyrrolidinyl)cyclohexyl]-benzeneacetamide;

(±)-4-bromo-N-methyl-N-[2-(N',N'-dimethylamino)-4-oxo-cyclohexyl]benzeneacetamide;

(±)-N-[4-acetyloxy-2-(1-pyrrolidinyl)cyclohexyl]-3,4-dichloro-N-methylbenzeneacetamide;

(±)-N-[4-acetyloxy-2-aminocyclohexyl]-3,4-difluoro-N-methylbenzeneacetamide;

(±)-3,4-dichloro-N-[5-(hydroxyimino)-2-(1-pyrrolidinyl)cyclohexyl]-N-methylbenzeneacetamide;

(±)-3,4-dichloro-N-[4,4-dimethoxy-2-(1-pyrrolidinyl)cyclohexyl]-N-methylbenzeneacetamide which can also be named:

(±)-3,4-dichloro-N-methyl-N-[4-oxo-2-(1-pyrrolidinyl)cyclohexyl]benzeneacetamide, dimethyl ketal;

(±)-3,4-dichloro-N-[5,5-diethoxy-2-(1-pyrrolidinyl)cyclohexyl]-N-methylbenzeneacetamide;

(±)-(1α, 2β)-3,4-dichloro-N-[4,4-dimethoxy-2-(1-pyrrolidinyl)cyclohexyl]-N-methylbenzeneacetamide;

(±)-4-trifluoromethyl-N-[4,4-dimethoxy-2-(1-pyrrolidinyl)cyclohexyl]-N-methylbenzeneacetamide;

(±)-3-trifluoromethyl-N-[4,4-diethoxy-2-(1-pyrrolidinyl)-cyclohexyl]-N-methylbenzeneacetamide;

(±)-3-hydroxy-4-methyl-N-[4,4-dimethoxy-2-(1-pyrrolidinyl)cyclohexyl]-N-methylbenzeneacetamide;

(±)-4-methanesulfonyl-N-[4,4-dimethoxy-2-(1-piperidinyl)-cyclohexyl]-N-methylbenzamide;

(±)-4-acetyloxy-N-[4,4-dimethoxy-2-(1-pyrrolidinyl)-cyclohexyl-N-methylbenzeneacetamide;

(±)-N-[4,4-bis(methylthio)-2-(1-pyrrolidinyl)cyclohexyl]-3,4-dichloro-N-methylbenzeneacetamide;

(±)-N-[5,5-bis(ethylthio)-2-(1-pyrrolidinyl)cyclohexyl]-3,4-di-chloro-N-methylbenzeneacetamide;

(±)-3,4-dichloro-N-[4-methylthio-2-(1-pyrrolidinyl)cyclohexyl]-N-methylbenzeneacetamide;

(±)-3,4-dichloro-N-[5-ethylthio-2-(1-pyrrolidinyl)cyclohexyl]-N-methylbenzeneacetamide;

(±)-3,4-dichloro-N-[6-methylthio-2-(1-pyrrolidinyl)cycloheptyl]-N-methylbenzeneacetamide;

(±)-3,4-dichloro-N-[4-mercapto-2-(1-pyrrolidinyl)cyclohexyl]-N-methylbenzeneacetamide;

[1R-(1α,2β,4β,5β)]-N-[4,5-dimethoxy-2-(1-pyrrolidinyl)cyclohexyl]-N-methyl-4-benzofuranacetamide;

[1S-(1α,2β,4β,5β)]-N-[4,5-dimethoxy-2-(1-pyrrolidinyl)cyclohexyl]-N-methyl-4-benzofuranacetamide;

[1R-(1α,2β,4α,5α)]-N-[4,5-dimethoxy-2-(1-pyrrolidinyl)cyclohexyl]-N-methyl-4-benzofuranacetamide;

[1S-(1α,2β,4α,5α)]-N-[4,5-dimethoxy-2-(1-pyrrolidinyl)cyclohexyl]-N-methyl-4-benzofuranacetamide;

[1R-(1α,2β,4β,5β)]-N-[4,5-dimethoxy-2-(1-pyrrolidinyl)cyclohexyl]-N-methylbenzo[b]thiophene-4-acetamide;

[1S-(1α,2β,4β,5β)]-N-[4,5-dimethoxy-2-(1-pyrrolidinyl)cyclohexyl]-N-methylbenzo[b]thiophene-4-acetamide;

[1R-(1α,2β,4α,5α)]-N-[4,5-dimethoxy-2-(1-pyrrolidinyl)cyclohexyl]-N-methylbenzo[b]thiophene-4-acetamide;

[1S-(1α,2β,4α,5α)]-N-[4,5-dimethoxy-2-(1-pyrrolidinyl)cyclohexyl]-N-methylbenzo[b]thiophene-4-acetamide;

[1R-(1α,2β,4β,5β)]-N-[4,5-dimethoxy-2-(1-pyrrolidinyl)cyclohexyl]-N-methyl-1-naphthaleneacetamide;

[1S-(1α,2β,4β,5β)]-N-[4,5-dimethoxy-2-(1-pyrrolidinyl)cyclohexyl]-N-methyl-1-naphthaleneacetamide;

[1R-(1α,2β,4α,5α)]-N-[4,5-dimethoxy-2-(1-pyrrolidinyl)cyclohexyl]-N-methyl-1-naphthaleneacetamide;

[1S-(1α,2β,4α,5α)]-N-[4,5-dimethoxy-2-(1-pyrrolidinyl)cyclohexyl]-N-methyl-1-naphthaleneacetamide;

[1R-(1α,2β,4β,5β)]-3,4-dichloro-N-[4,5-dimethoxy-2-(1-pyrrolidinyl)cyclohexyl]-N-methybenzeneacetamide;

[1S-(1α,2β,4β,5β)]-3,4-dichloro-N-[4,5-dimethoxy-2-(1-pyrrolidinyl)cyclohexyl]-N-methybenzeneacetamide;

[1R-(1α,2β,4α,5α)]-3,4-dichloro-N-[4,5-dimethoxy-2-(1-pyrrolidinyl)cyclohexyl]-N-methylbenzeneacetamide;

[1S-(1α,2β,4α,5α)]-3,4-dichloro-N-[4,5-dimethoxy-2-(1-pyrrolidinyl)cyclohexyl]-N-methylbenzeneacetamide;

[1R-(1α,2β,4β,5β)]-N-[4,5-dimethoxy-2-(1-pyrrolidinyl)cyclohexyl]-N-methyl-9H-fluorene-9-carboxamide;

[1S-(1α,2β,4β,5β)]-N-[4,5-dimethoxy-2-(1-pyrrolidinyl)cyclohexyl]-N-methyl-9H-fluorene-9-carboxamide;

[1R-(1α,2β,4α,5α)]-N-[4,5-dimethoxy-2-(1-pyrrolidinyl)cyclohexyl]-N-methyl-9H-fluorene-9-carboxamide;

[1S-(1α,2β,4α,5α)]-N-[4,5-dimethoxy-2-(1-pyrrolidinyl)cyclohexyl]-N-methyl-9H-fluorene-9-carboxamide;

(±)-(1α,2β,4β)-N-methyl-N-[4-methoxy-2-(1-pyrrolidinyl)cyclohexyl]-4-benzofuranacetamide;

(±)-(1α,2β,4α)-N-methyl-N-[4-methoxy-2-(1-pyrrolidinyl)cyclohexyl]-4-benzofuranacetamide;

(±)-(1α,2β,5β)-N-methyl-N-[5-methoxy-2-(1-pyrrolidinyl)cyclohexyl]-4-benzofuranacetamide;

(±)-(1α,2β,5α)-N-methyl-N-[5-methoxy-2-(1-pyrrolidinyl)cyclohexyl]-4-benzofuranacetamide;

(±)-(1α,2β,4α)-N-[4-methoxy-2-(1-pyrrolidinyl)cyclohexyl]-N-methyl-9H-fluorene-9-carboxamide;

(±)-(1α,2β,5β)-N-[5-methoxy-2-(1-pyrrolidinyl)cyclohexyl]-N-methyl-9H-fluorene-9-carboxamide;

(±)-N-methyl-2-(1-naphthalenyloxy)-N-[2-(1-pyrrolidinyl)cyclohexyl]acetamide;

(±)-N-methyl-2-(2-naphthalenyoxy)-N-[2-(1-pyrrolidinyl)cyclohexy]acetamide;

(±)-1,2-dihydro-N-methyl-N-[2-(1-pyrrolidinyl)cyclohexyl]-1-acenaphthylencarboxamide, (isomer I, mixture of (1α, 2β) and (1β,2α) forms);

(±)-1,2-dihydro-N-methyl-N-[2-(1-pyrrolidinyl)cyclohexyl]-1-acenaphthylenecarboxamide, (isomer II, mixture of (1α, 2β) and (1β,2α) forms);

(±)-N-[4,5-dimethoxy-2-(1-pyrrolidinyl)cyclohexyl]-1,2-dihydro-N-methyl-1-acenaphthylenecarboxamide (isomer I, mixture of (1α,2β, 4β, 5β) and (1β, 2α, 4α, 5α forms);

(±)-N-[4,5-dimethoxy-2-(1-pyrrolidinyl)cyclohexyl]-1,2-dihydro-N-methyl-1-acenaphthylenecarboxamide (isomer II, mixture of (1α,2β, 4β, 5β) and (1β, 2α, 4α, 5α forms);

(±)-1,2-dihydro-N-[4-methoxy-2-(1-pyrrolidinyl)cyclohexyl]-N-methyl-1-acenaphthylenecarboxamide (isomers I and II, mixtures of (1α,2β, 4β) and (1β, 2α, 4α) forms);

(±)-1,2-dihydro-N-[4-methoxy-2-(1-pyrrolidinyl)cyclohexyl]-N-methyl-1-acenaphthylenecarboxamide (isomers I and II, mixtures of (1β, 2α, 4α) and (1α,2β, 4β) forms);

(±)-trans-N-methyl-N-[2-(1-pyrrolidinyl)cyclohexyl]-9H-fluorene-9-carboxamide;

(±)-trans-1,3-dihydro-N-methyl-1-oxo-N-[2-(1pyrrolidinyl)cyclohexyl]-4-isobenzofuranacetamide;

(±)-(1α, 2β, 4β, 5β)-N-[4,5-dimethoxy-2-(1-pyrrolidinyl)cyclohexyl]-1,3-dihydro-N-methyl-1-oxo-4-isobenzofuranacetamide;

(±)-(5α,7α, 8β)-3,4-dichloro-N-methyl-N-[7-(1-pyrrolidinyl)-1-oxaspiro[4.5]dec-8-yl]benzeneacetamide;

(±)-(5α,7α, 8β)-bromo-N-methyl-N-[7-(1-pyrrolidinyl)-1-oxaspiro[4.5]dec-8yl]benzeneacetamide;

(±)-(5α,7α, 8β)-4-methoxy-N-methyl-N-[7-(1-pyrrolidinyl)-1-oxaspiro[4.5]dec-8-yl]benzeneacetamide;

(±)-(5α,7α, 8β)-N-methyl-2-nitro-N-[7-(1-pyrrolidinyl)-1-oxaspiro[4.5]dec-8-yl]benzeneacetamide;

(±)-(5α,7α, 8β)-N-methyl-3-nitro-N-[7-(1-pyrrolidinyl)-1-oxaspiro[4.5]dec-8-yl]benzeneacetamide;

(±)-(5α,7α, 8β)-N-methyl-4-nitro-N-[7-(1-pyrrolidinyl)-1-oxaspiro[4.5]dec-8-yl]benzeneacetamide;

(±)-(5α,7α, 8β)-N-methyl-N-[7-(1-pyrrolidinyl)-1-oxaspiro[4.5]dec-8-yl-3-(trifluoromethyl)benzeneacetamide;

(±)-(5α,6α, 7β)-3,4-dichloro-N-methyl-N-[7-(1-pyrrolidinyl)-1-oxaspiro[4.5]dec-6-yl]benzeneacetamide;

(±)-(5α,7α, 8β)-3,4-dichloro-N-methyl-N-[7-(1-pyrrolidinyl)-1-thiaspiro[4.5]dec-8-yl]benzeneacetamide;

(±)-(5α,7β, 8α)-3,4-dichloro-N-methyl-N-[8-(1-pyrrolidinyl)-1-oxaspiro[4.5]dec-7-yl]benzeneacetamide;

(±)-(5α,7α, 8β)-3,4-dichloro-1,N-dimethyl-[7-(1-pyrrolidinyl)-1-azaspiro[4.5]dec-8yl]benzeneacetamide;

(±)-(5α,7α, 8β)-4-bromo-N-methyl-N-[7-(1-pyrrolidinyl)-1-azaspiro[4.5]dec-8-yl]benzamide;

(±)-(5α,7α, 8β)-3,4-dichloro-N-methyl-N-[7-(1-pyrrolidinyl)-1-thiaspiro[4.5]dec-8-yl]benzamide;

(±)-(5α,7α, 8β)-3,4-dichloro-N-methyl-N-[7-(1-pyrrolidinyl)-1-thiaspiro[4.5]dec-8-yl]benzeneacetamide;

(±)-(5α,7α, 8β)-3,4-dichloro-N-methyl-N-[7-(1-pyrrolidinyl)-1-thiaspiro[4.5]dec-8-yl]benzeneacetamide, 1-oxide;

(±)-(5α,7α, 8β)-3,4-dichloro-N-methyl-N-[7-(1-pyrrolidinyl)-1-thiaspiro[4.5]dec-8-yl]benzeneacetamide, 1,1-dioxide;

(±)-(5α,7α, 8β)-N-methyl-N-[7-(1-pyrrolidinyl)-1-azaspiro[4.5]dec-8-yl]4-trifluoromethylbenzeneacetamide;

(±)-(5α,7α, 8β)-N-methyl-N-[8-(1-pyrrolidinyl)-1-thiaspiro[4.5]dec-7-yl]-3-trifluoromethylbenzeneacetamide;

[5R-(5α,7α,8β)]-N-Methyl-[7-(1-pyrrolidinyl)-1-oxaspiro[4.5]dec-8-yl]-1H-indene-3-acetamide;

[5S-(5α,7α,8β)]-N-Methyl-[7-(1-pyrrolidinyl)-1-oxaspiro[4.5]dec-8-yl]-1H-indene-3-acetamide;

[5R-(5α,7β,8α)]-N-Methyl-[7-(1-pyrrolidinyl)-1-oxaspiro[4.5]dec-8-yl]-1H-indene-3-acetamide;

[5S-(5α,7β,8α)]-N-Methyl-[7-(1-pyrrolidinyl)-1-oxaspiro[4.5]dec-8-yl]-1H-indene-3-acetamide;

[5R-(5α,7α,8β)]-N-Methyl-N-[7-(1-pyrrolidinyl)-1-oxaspiro[4.5]dec-8-yl]-1H-indole-3-acetamide;

[5S-(5α,7α,8β)]-N-Methyl-N-[7-(1-pyrrolidinyl)-1-oxaspiro[4.5]dec-8-yl]-1H-indole-3-acetamide;

[5R-(5α,7β,8α)]-N-Methyl-N-[7-(1-pyrrolidinyl)-1-oxaspiro[4.5]dec-8-yl]-1H-indole-3-acetamide;

[5S-(5α,7β,8α)]-N-Methyl-N-[7-(1-pyrrolidinyl)-1-oxaspiro[4.5]dec-8-yl]-1H-indole-3-acetamide;

[5R-(5α,7α,8β)]-N-Methyl-N-[7-(1-pyrrolidinyl)-1-oxaspiro[4.5]dec-8-yl]-2-benzofuranacetamide;

[5S-(5α,7α,8β)]-N-Methyl-N-[7-(1-pyrrolidinyl)-1-oxaspiro[4.5]dec-8-yl]-2-benzofuranacetamide;

[5R-(5α,7β,8α)]-N-Methyl-N-[7-(1-pyrrolidinyl)-1-oxaspiro[4.5]dec-8-yl]-2-benzo[b]furanacetamide;

[5S-(5α,7β,8α)]-N-Methyl-N-[7-(1-pyrrolidinyl)-1-oxaspiro[4.5]dec-8-yl]-2-benzo[b]furanacetamide;

[5R-(5α,7β,8β)]-N-Methyl-N-[7-(1-pyrrolidinyl)-1-oxaspiro[4.5]dec-8-yl]-3-benzo[b]furanacetamide;

[5S-(5α,7α,8β)]-N-Methyl-N-[7-(1-pyrrolidinyl)-1-oxaspiro[4.5]dec-8-yl]-3-benzo[b]furanacetamide;

[5R-(5α,7β,8α)]-N-Methyl-N-[7-(1-pyrrolidinyl)-1-oxaspiro[4.5]dec-8-yl]-3-benzo[b]furanacetamide;

[5S-(5α,7β,8α)]-N-Methyl-N-[7-(1-pyrrolidinyl)-1-oxaspiro[4.5]dec-8-yl]-3-benzo[b]furanacetamide;

[5R-(5α,7α,8β)]-N-Methyl-N-[7-(1-pyrrolidinyl)-1-oxaspiro[4.5]dec-8-yl]-4-benzo[b]furanacetamide;

[5S-(5α,7α,8β)]-N-Methyl-N-[7-(1-pyrrolidinyl)-1-oxaspiro[4.5]dec-8-yl]-4-benzo[b]furanacetamide;

[5R-(5α,7β,8α)]-N-Methyl-N-[7-(1-pyrrolidinyl)-1-oxaspiro[4.5]dec-8-yl]-4-benzo[b]furanacetamide;

[5S-(5α,7β,8α)]-N-Methyl-N-[7-(1-pyrrolidinyl)-1-oxaspiro[4.5]dec-8-yl]-4-benzo[b]furanacetamide;

[5R-(5α,7α,8β)]-N-Methyl-N-7-(1-pyrrolidinyl)-1-oxaspiro[4.5]dec-8-yl]-4-benzo[b]thiophene-4-acetamide;

[5S-(5α,7α,8β)]-N-Methyl-N-7-(1-pyrrolidinyl)-1-oxaspiro[4.5]dec-8-yl-4-benzo[b]thiophene-4-acetamide;

[5R-(5α,7β,8α)]-N-Methyl-N-7-(1-pyrrolidinyl)-1-oxaspiro[4.5]dec-8-yl-4-benzo[b]thiophene-4-acetamide;

[5S-(5α,7β,8α)]-N-Methyl-N-7-(1-pyrrolidinyl)-1-oxaspiro[4.5]dec-8-yl-4-benzo[b]thiophene-4-acetamide;

Also included but are not limited to:

(−)-(5α,7α,8β)]-N-Methyl-N-[7-(1-pyrrolidinyl)-1-oxaspiro[4.5]dec-8-yl]-4-benzo[b]furanacetamide;

(−)-(5α,7α,8β)]-N-7-(1-pyrrolidinyl)-1-oxaspiro[4.5]dec-8-yl-4-benzo[b]thiophene-4-acetamide;

(±)-(5α,6α,7β)-3,4-dichloro-N-methyl-N-[7-(1-pyrrolidinyl)-2-oxaspiro[4.5]dec-6-yl]benzeneacetamide;

(±)-(5α,6α,7β)-3,4-dichloro-N-methyl-N-[6-(1-pyrrolidinyl)-2-oxaspiro[4.5]dec-7-yl]benzeneacetamide; and (±)-(5α,7α,8β)-3,4-dichloro-N-methyl-N-[8-(1-pyrrolidinyl)-2-oxaspiro[4.5]dec-7-yl]benzeneacetamide.

The compounds of Formula II and Formula IIa have the following structure:

wherein for the enantiomers and racemic mixtures
n is 0 or 1;
A is $$-\underset{R^4}{\underset{|}{C}}-$$

or,

—CH$_2$CH$_2$— provided that in Formula II, when n is 1, A may also be —O— or —S—;

B, C and D are independently selected from the group consisting of H, OH, OCOR$^5$, OCH$_2$CH$_2$OR$^5$, OR$^6$, R$^6$, CH$_2$OR$^6$, CH$_2$COR$^7$, Cl, F, Br, I, NH$_2$, NHR$^8$, NR$^8$R$^9$, SH, SR$^6$, CH$_2$SR$^6$ and OC(S)N(CH$_3$)$_2$; or two of B, C and D when on adjacent carbon atoms taken together form a fused benzo ring;

X and Y are independently selected from the group consisting of H, OCH$_3$, Cl, F, Br, I, NO$_2$, CF$_3$, CN, SO$_2$R$^{10}$, and SO$_2$CF$_3$; or X and Y taken together with the benzene ring form <chemical structure: benzothiophene>

R and R$^1$ independently are selected from the group consisting of H, and alkyl of 1 to 3 carbon atoms;

R$^2$ is H; alkyl of 1 to 6 carbon atoms; CH$_2$CF$_3$; alkenylmethyl of 3 to 6 carbon atoms; hydroxyalkenylmethyl of 2 to 5 carbon atoms; cycloalkyl of 3 to 6 carbon atoms; cyclopropylmethyl; cyclobutylmethyl, or phenylalkyl of 7 to 9 carbon atoms; or R$^2$ can be taken together with R$^1$ and the nitrogen to which they are attached to be 1-azetidinyl; 1-pyrrolidinyl optionally substituted at the 3-position by OH, alkyl of 1 to 3 carbon atoms, alkoxy of 1 to 3 carbon atoms or alkanoyloxy of 1 to 3 carbon atoms; 1-piperazinyl optionally substituted at the 4-position by alkyl of 1 to 3 carbon atoms; 1-morpholino; 2,5-dihydro-1H-pyrrol-1-yl; 3-azabicyclo[3.1.0]hexan-3-yl; or 3-azabicyclo[3.2.0]heptan-3-yl;

R$^3$ is H, but if n is 1 and A is CH$_2$, R$^3$ may also be CH$_3$, CH$_2$OH, CHO, or COR$^{11}$;

R$^4$ is H, alkyl of 1 to 6 carbon atoms, —CH$_2$OH—, CHO, or COR$^{12}$;

R$^5$ is alkyl of 1 to 6 carbon atoms, phenyl, or monosubstituted phenyl;

R$^6$, R$^8$, R$^9$, R$^{10}$ and R$^{13}$ are independently an alkyl group of 1 to 3 carbon atoms; and R$^7$, R$^{11}$ and R$^{12}$ independently are selected from the group consisting of H, OH, OR$^{13}$, NHR$^{13}$, and NR$_2^{13}$; or a stable N-oxide or a pharmaceutically acceptable salt thereof.

Preferred compounds are those of Formula IIb, particularly those having the formula wherein
n is 1;
A is —CH$_2$—, —O—, or —S—;
B is OH, OCOR$^5$, OCH$_2$CH$_2$OR$^5$, OR$^6$, CH$_2$OR$^6$, or CH$_2$COR$^7$;
C is H, OH, or OR$^6$; and
R$^1$ and R$^2$ independently are selected from H or alkyl of 1 to 3 carbon atoms or are taken together with the nitrogen to which they are attached to form the group 1-azetidinyl, 1-pyrrolidinyl, 1-(2,5-dihydro-1H-pyrrolyl) or 1-piperidinyl.

More preferred are compounds of Formula IIb wherein A is —CH$_2$—.

Specifically preferred compounds include:

(±)trans-3,4-dichloro-N-methyl-N-[2-(pyrrolidin-1-yl)-5-methoxy-1,2,3,4-tetrahydronaphth-1-yl]-benzeneacetamide hydrochloride or the methansulfonic acid salt;

(±)trans-3,4-dichloro-N-methyl-N-[2-(pyrrolidin-1-yl)-1,2,3,4-tetrahydronaphth-1-yl]-benzeneacetamide hydrochloride;

(±)trans-3,4-dichloro-N-methyl-N-[2-(pyrrolidin-1-yl)-6-methoxy-1,2,3,4-tetrahydronaphth-1-yl]-benzeneacetamide hydrochloride;

(±)trans-3,4-dichloro-N-methyl-N-[2-(pyrrolidin-1-yl)-6-hydroxy-1,2,3,4-tetrahydronaphth-1-yl]-benzeneacetamide hydrochloride;

(±)-trans-3,4-dichloro-N-methyl-N-[2-(pyrrolidin-1-yl)-1,2,3,4-tetrahydronaphth-1-yl]-benzeneacetamide hydrochloride;

(±)trans-3,4-dichloro-N-methyl-N-[2,3-dihydro-2-(pyrrolidin-1-yl)-1H-inden-1-yl]-benzeneacetamide hydrochloride;

(±)trans-3,4-dichloro-N-methyl-N-[3,4-dihydro-3-(pyrrolidin-1-yl)-2H-benzopyran-4-yl]-benzeneacetamide hydrochloride;

(±)trans-3,4-dichloro-N-methyl-N-[2-(pyrrolidin-1-yl)-5-hydroxy-1,2,3,4-tetrahydronaphth-1-yl]-benzeneacetamide hydrochloride;

(±)trans-3,4-dichloro-N-methyl-N-[2-(pyrrolidin-1-yl)-5-propionyloxy-1,2,3,4-tetrahydronaphth-1-yl]-benzeneacetamide hydrochloride;

(±)trans-3,4-dichloro-N-methyl-N-[2-(pyrrolidin-1-yl)-5-benzoyloxy-1,2,3,4-tetrahydronaphth-1-yl]-benzeneacetamide hydrochloride;

(±)trans-3,4-dichloro-N-methyl-N-[2-(pyrrolidin-1-yl)-6,7-dihydroxy-1,2,3,4-tetrahydronaphth-1-yl]-benzeneacetamide hydrochloride;

(±)trans-N-methyl-N-[3,4-dihydro-3-(pyrrolidin-1-yl)-2H-benzopyran-4-yl]-benzeneacetamide hydrochloride;

(±)trans-3,4-dichloro-N-methyl-N-[3,4-dihydro-8-methoxy-3-(pyrrolidin-1-yl)-2H-benzopyran-4-yl]-benzeneacetamide hydrochloride;

(±)trans-3,4-dichloro-N-methyl-N-[2-(pyrrolidin-1-yl)-5-(N,N-dimethylthiocarbamoyloxy)-1,2,3,4-tetrahydronaphth-1-yl]-benzeneacetamide hydrochloride;

(±)trans-3,4-dichloro-N-methyl-N-[2-(2,5-dihydro-1H-pyrrol-1-yl)-5-methoxy-1,2,3,4-tetrahydronaphth-1-yl]-benzeneacetamide hydrochloride, and (±)trans-3-nitro-N-methyl-N-[2,3-dihydro-2-(pyrrolidin-1-yl)-1H-inden-1-yl]-benzeneacetamide hydrochloride.

Compounds of Formula III have the following structure:

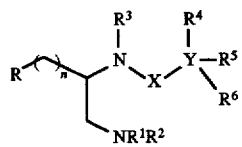

wherein n is 0–1; and

R is unsubstituted phenyl or phenyl substituted with one to three substituents selected from the group consisting of halogen, $C_{1-6}$ alkyl, hydroxy, —O—CO—$NH_2$, —O—CO—NHalkyl, —O—CO—N(alkyl)$_2$, $Cl_{1-6}$ alkoxy, trifluoromethyl, $C_{1-4}$-alkoxy-$C_{1-4}$ alkyloxy, carboxy-$C_{1-4}$ alkyloxy, nitrile, nitro and amino; or mono or dialkyl amino, amide, sulfonamide, carboxamide; or mono or disubstituted carboxamide, ureido; or mono and di-alkylsubstituted ureido; or R represents an alkyl or cycloalkyl group having up to 7 carbon atoms. The cycloalkyl moiety, where present, can be optionally substituted by one or more substituents selected from the group consisting of from hydroxy, amino, amidino, guanidino, aminocarbonyl, carboxy, $C_{1-6}$ alkoxy, ($C_{1-6}$ alkoxy)carbonyl, ($C_{3-6}$ alkenyloxy)carbonyl, ($C_{3-6}$ alkynyloxy)carbonyl, $C_{1-6}$ alkanoyloxy, $C_{1-6}$ alkylsulfide, $C_{1-6}$ alkylsulfoxide, $C_{1-6}$ alkylsulfone, $C_{1-6}$(monoalkylamino)carbonyl, $C_{1-6}$ acylamino, $C_{1-6}$ acylmethylamino and $C_{1-6}$ monoalkylamino; or R represents the group —B—$R^7$ in which B represents —$CH_2$—, —CH($CH_3$)— or a single bond and $R^7$ represents an optionally substituted $C_{6-10}$ carbocyclic aryl group with one to three substituents selected from the group consisting of halogen, $C_{1-6}$ alkyl, hydroxy, —O—CO—$NH_2$, —O—CO—NHalkyl, —O—CO—N(alkyl)$_2$, $C_{1-6}$ alkoxy, trifluoromethyl, $C_{1-4}$-alkoxy-$C_{1-4}$ alkyloxy, carboxy-$C_{1-4}$ alkyloxy, nitrile, nitro and amino; or mono or dialkyl amino, amide, sulfonamide or carboxamide; mono or disubstituted carboxamide or ureido; and mono or di-alkylsubstituted ureido; or R represents the group —D—$R^8$ in which D represents a single bond, —$CH_2$—, —CH($CH_3$)—, —$CH_2$O—, —CH($CH_3$)O—, —$CH_2$S—, —CH($CH_3$)S—, —$CH_2$NH— or —CH($CH_3$)NH— and $R^8$ represents a 4–6 membered heterocyclic ring containing up to 4 heteroatoms selected from the group consisting of oxygen, sulfur and nitrogen, the heterocyclic ring optionally being substituted on nitrogen or sulfur by oxygen or on nitrogen by hydroxy or $C_{1-3}$ alkyl and/or the ring optionally being substituted on carbon by one or more substituents selected from the group consisting of amino, hydroxy, thio (and their tautomers), cyano, halogen, $C_{1-3}$ alkoxy, $C_{1-3}$ monoalkylamino, $C_{1-3}$ acylamino, $C_{1-3}$ acylmethylamino, and $C_{1-3}$ alkylthio;

$R^1$ and $R^2$ are independently selected from the group consisting of H, $C_{1-6}$ alkyl, $C_{3-5}$ alkenyl, $C_{3-5}$ alkynyl, and $C_{4-7}$ cycloalkylalkyl group; or $R^2$ can be taken together with $R^1$ and the nitrogen to which they are attached to form a heterocyclic ring which may optionally contain a further heteroatom selected from the group consisting of oxygen, nitrogen, and sulfur (i.e. 1-azetidinyl; 1-pyrrolidinyl optionally substituted at the 3-position by OH, —$CH_2$OH, tri($C_1$–$C_6$ alkyl)silyloxy, acyloxy, $C_{1-6}$ alkyl, $C_{1-6}$ alkoxy or $C_{1-6}$ alkanoyloxy; 1-piperazinyl optionally substituted at the 4-position by alkyl of 1 to 3 carbon atoms; 1-morpholino; 2,5-dihydro-1H-pyrrol-1-yl; 3-azabicyclo[3.1.0]hexan-3-yl; or 3-azabicyclo[3.2.0]heptan-3-yl);

$R^3$ represents hydrogen, $C_{1-7}$ alkyl, —$CH_2$-phenyl or heterocyclic (the phenyl or heterocyclic substituted with one to three substituents selected from the group consisting of halo, $C_{1-4}$ alkyl, $C_{1-4}$ alkoxy and methoxycarbonyl; mono-, di- or tri-halomethyl; cyano; $COR^9$; CH=$NOR^{10}$; $OR^{10}$; $SR^{10}$; $CH_2$CN; $CH_2OR^{10}$; $CH_2SR^{10}$; $CH_2S(O)R^{10}$; $CH_2S(O)_2R^{10}$; $CH_2N(R^{10})R^{11}$; $CH_2(R^{10})R^{11}$; $CH_2NR^{10}$OH; $CH_2N(COR^{10})$OH; $CH_2NR^{10}COR^{11}$; $CH_2NR^{10}S(O)_2R^{11}$; or $CH_2OCOR^{10}$, wherein $R^9$ is hydrogen, hydroxy, amino, NHOH, $NHOCH_3$, pyridylamino, NHN($CH_3$)$_2$, $C_{1-4}$ alkoxy, benzyloxy, $C_{-4}$ alkylamino, di-$C_{1-4}$ alkylamino, $C_{1-4}$ alkyl or $C_{1-4}$ alkylthio; $R^{10}$ and $R^{11}$ are each hydrogen, $C_{1-4}$ alkyl, $C_{1-4}$ alkoxy or $C_{7-11}$ phenylalkyl), or $OR^{12}$, wherein $R^{12}$ is hydrogen, $C_{1-4}$ alkyl or a hydroxy protecting group;

X represents —CO—, or —$SO_2$—; and

Y represents a single bond (in this case, only one of $R^4$–$R^6$ is attached), a tetrahedral carbon, —OC—, —SC—, —S(O)C—, —S(O)$_2$C—, or —$CH_2$C—; and $R^4$, $R^5$, and $R^6$ are independently selected from the group consisting of hydrogen, hydroxy, alkoxy, $C_{1-4}$ alkylenedioxy, $C_{1-8}$ cyclic and acyclic alkyl; substituted or unsubstituted carbocyclic aromatic or heterocyclic aromatic group (i.e. phenyl, naphthyl, biphenyl, indanyl, 1-tetralone-6-yl, furyl, thienyl, pyridyl, thiazolyl, benzofuryl or benzothienyl, substituted with one to three substituents selected from the group consisting of halo, cyano, —$OCONH_2$, —OCONHalkyl, —OCON(alkyl)$_2$, —OCOalkyl, —NHCHO, —NHCOalkyl, ureido, —NHCONHalkyl, —NalkylCONHalkyl, —NHCON(alkyl)$_2$, —NalkylCON(alkyl)$_2$, —$NHSO_2$alkyl, —COalkyl, —$CONH_2$, —CONHalkyl, —CON(alkyl)$_2$, —$CH_2CONH_2$, —$CH_2$CONHalkyl, —$CH_2$CON(alkyl)$_2$, —$OCH_2$CONH, —$OCH_2$CONHalkyl, —$OCH_2$CON(alkyl)$_2$, $C_{1-4}$ alkyl, $C_{1-4}$ alkoxy, amino, hydroxy, nitro, trifluoromethyl, —$SO_2$alkyl, —SOalkyl, and mesyl; or $R^5$ and $R^6$ can together form the following structure

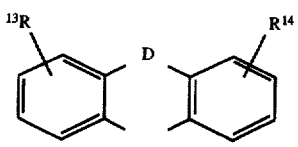

wherein $R^{13}$ and $R^{14}$ are independently selected from the group consisting of hydrogen, halogen, hydroxy, alkoxy, mono-, di- or tri-halomethyl, amino, —NHalkyl, —N(alkyl)$_2$, —NHCOalkyl, ureido, nitro, and methylenedioxy; and D represents —CH$_2$—, —O—, —S—, —NH, —CH$_2$CH$_2$—, —CH=CH—, —CH$_2$NH—, or —CH$_2$Nalkyl-.

Preferred examples include the following compounds:

N-methyl-N-{[1S]-1-phenyl-2-[(3S)-(3-hydroxypyrrolidin-1-yl)]ethyl}-2,2-diphenylacetamide hydrochloride, 3,4-dichloro-N-methyl-N-[(1S)-1-phenyl-2-(1-pyrrolidinyl)ethyl]benzeneacetamide hydrochloride, N-methyl-N-{[1S]-1-phenyl-2-[(3S)-(3-hydroxypyrrolidin-1-yl)]ethyl}-2-aminophenylacetamide hydrochloride, 3,4-dichloro-N-methyl-N-[(1S)-1-isopropyl-2-(1-pyrrolidinyl)ethyl]benzeneacetamide hydrochloride, 3,4-dichloro-N-methyl-N-[(1S)-1-(O-acetic acid-3-hydroxyphenyl)-2-(1-pyrrolidinyl)ethyl]benzeneacetamide hydrochloride, and N-methyl-N-[(1S)-1-phenyl-2-(1-pyrrolidinyl)ethyl]-2,2-diphenylacetamide hydrochloride The compounds of Formula IV have the following structure:

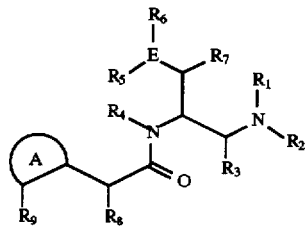

IV wherein:

$R_1$ and $R_2$ are the same or different and are hydrogen, $C_{1-6}$ alkyl $C_{3-6}$ alkenyl, $C_{3-6}$ cycloalkyl or $C_{4-12}$ cycloalkylalkyl groups, or together form a $C_{2-8}$ branched or linear polymethylene or $C_{2-6}$ alkenylene group, optionally substituted with a hetero-atom; or —NR$_1$R$_2$ form a 5-membered (optionally containing an oxygen atom adjacent to the nitrogen) or 6-membered ring, which ring optionally contains one unit of unsaturation and which is unsubstituted or substituted with hydroxy, $C_{1-6}$ acyloxy, oxo, optionally substituted methylene, —COR$_{10}$(where $R_{10}$ represents $C_{1-6}$ alkyl, —OR$_{11}$ or —NH R$_{11}$ and $R_{11}$ represents hydrogen, $C_{1-6}$ alkyl, aryl, or Ar($C_{1-6}$)alkyl, or N=NOR$_{12}$ (where $R_{12}$ represents $C_{1-6}$ alkyl);

$R_3$ is hydrogen, $C_{1-6}$ alkyl or phenyl; or $R_3$ together with $R_1$ forms a —(CH$_2$)$_3$— or —(CH$_2$)$_4$— group;

$R_4$ is $C_{1-6}$ alkyl, or phenyl;

$R_5$ is hydrogen, or together with $R_4$ forms a $C_{2-5}$ linear polymethylene group;

$R_6$ represents hydroxy, $C_{1-6}$ alkyl, $C_{1-6}$ hydroxyalkyl, $C_{1-6}$ carboxyalkyl, phenyl, oxo, amino, carboxy, amido, —COR$_{13}$, —CO$_2$R$_{13}$ or —COCO$_2$R$_{13}$ (where $R_{13}$ represents a hydrogen atom or an unsubstituted or substituted $C_{1-10}$ hydrocarbon moiety); —NRxCORx (where Rx represents $C_{1-6}$ alkyl), optionally substituted ethylene; or $R_6$ together with the E atom to which it is attached, forms a 5 or 6-membered ring containing one or more heteroatoms; $R_7$ is hydrogen, or together with $R_6$ forms an optionally substituted or unsubstituted single or fused aryl or heterocyclic ring, containing from 5 to 12 ring atoms and comprising up to four heteroatoms in the ring selected from the group consisting of oxygen, nitrogen and sulphur, which may be substituted with hydrogen, $C_{1-6}$ alkyl, —CH$_2$OR$_{14}$, halogen, hydroxy, $C_{1-6}$ alkoxy, $C_{1-6}$ alkoxycarbonyl, thiol, $C_{1-6}$ alkylthio, —OCOR$_{15}$, —NHCOR$_{16}$, —NHSO$_2$R$_{17}$ or —CH$_2$SO$_2$NR$_{18}$R$_{19}$, in which each of $R_{14}$ to $R_{19}$ is independently hydrogen, $C_{1-6}$ alkyl, aryl or aralkyl. A is aryl or heteroaryl ring, optionally mono or disubstituted with $C_{1-6}$ alkyl, $C_{2-6}$ alkenyl, $C_{1-6}$ haloalkyl, $C_{2-6}$ haloalkenyl, $C_{2-6}$ haloalkynyl, aryl, aralkyl, hydroxy, $C_{1-6}$ alkoxy, $C_{1-6}$ haloalkoxy, thiol, $C_{1-6}$ alkylthio, $C_{1-6}$ haloalkylthio, halogen, nitro, cyano, carboxy, aryloxy, aralkoxycarbonyl, carbamoyl, sulfonyl or sulfamoyl;

E represents methylene, sulphur, oxygen or an imino;

$R_8$ is hydrogen or $C_{1-6}$ alkyl; and $R_9$ is hydrogen or together with $R_8$ may form the group —(CRaRa)m-C(=Y)— wherein Ra is hydrogen or $C_{1-6}$ alkyl having up to a maximum of 3 alkyl groups;

m is 1, 2, or 3; and

Y represents two hydrogens or oxygen.

Preferred compounds of Formula IV include the following:

(±)1-(Pyrrolidin-1-yl)methyl-2-(3,4-dichlorophenyl)-acetyl-4,4-dimethyl-1,2,3,4-tetrahydroisoquinoline;

(±)8-[(3,4-Dichlorophenyl)acetyl]-7-(1-pyrrolidinylmethyl)-1,4-dioxa-8-aza[4.5]spirodecane;

(±)Methyl 4-[3,4-dichlorophenyl)acetyl]-3-(1-pyrrolidinylmethyl)-1-piperazinecarboxylate 1-[(3,4-Dichlorophenyl)acetyl]-2-[(3-oxo-1-pyrolidinyl)methyl]-piperidine;

(±)[S-(RR)]-(—)5-[(3,4-Dichlorophenyl)acetyl]-4,5,6,7-tetrahydro-4[(3-hydroxy-1-pyrolidinyl)methyl]furo[3,2-c]pyridine;

(±)[S-(RS)]-4-Acetyl-1-[(3,4-dichlorophenyl)acetyl]-2-[(3-hydroxy-1-pyrolidinyl)methyl]pyridine;

(±)2-[(3,4-Dichlorophenyl)acetyl]-1,2,3,4-tetrahydro-1-(1-pyrolidinyl)methyl)-5-isoquinolinol;

(±)4-(Pyrolidin-1-yl)methyl-5-(3,4-dichlorophenyl)acetyl-4,5,6,7-tetrahydrothieno[3,2,-c]pyridine;

(±)1-[(5,6-Dichloro-3-oxoindan-1-carbonyl)-2-pyrrolidin-1-ylmethyl)piperidine;

(±)2-(3,4-Dichlorophenyl)acetyl-3-(pyridin-1-yl)methyl-decahydroisoquinoline; and (±)1-(4-Trifluoromethylphenyl)acetyl-2-(3-hydroxypyrolidin-1-yl)methyl-4,4-dimethyl piperidine.

The compounds of Formula V have the following structure:

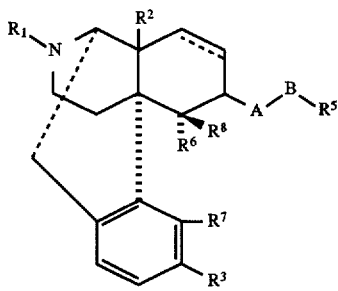

wherein

——— represents a single or double bond;

R¹ represents an alkyl group having 1–5 carbon atoms, a cycloalkylalkyl group having 4–7 carbon atoms, a cycloalkenylalkyl group having 5–7 carbon atoms, an aryl group having 6–12 carbon atoms, an aralkyl group having 7–13 carbon atoms, an alkenyl group having 4–7 carbon atoms, an allyl group, a furan-2-ylalkyl group having 1–5 carbon atoms, or a thiophen-2-ylalkyl group having 1–5 carbon atoms;

R² represents a hydrogen atom, a hydroxy group, a nitro group, an alkanoyloxy group having 1–5 carbon atoms, an alkoxy group having 1–5 carbon atoms, an alkyl group having 1–5 carbon atoms, or —NR⁹R¹⁰ wherein R⁹ represents a hydrogen atom or an alkyl group having 1–5 carbon atoms, and R¹⁰ represents a hydrogen atom; an alkyl group having 1–5 carbon atoms, or —C(=O)R¹¹ wherein R¹¹ represents a hydrogen atom, a phenyl group or an alkyl group having 1–5 carbon atoms;

R³ represents a hydrogen atom, a hydroxy group, an alkanoyloxy group having 1–5 carbon atoms, or an alkoxy group having 1–5 carbon atoms;

A represents —XC(=Y)—, —XC(=Y)Z—, —X—, —XSO₂—, or —OC(OR⁴)R⁴— (where, X, Y and Z each independently represent NR⁴, S or O wherein R⁴ represents a hydrogen atom, a straight-chain or branched chain alkyl group having 1–5 carbon atoms or an aryl group having 6–12 carbon atoms, and wherein R⁴ may be identical or different;

B represents a valence bond, a straight-chain or branched chain alkylene group having 1–14 carbon atoms (which may be substituted with at least one substituent selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein 1 to 3 methylene groups may be replaced with carbonyl groups), an acyclic unsaturated hydrocarbon containing from 1 to 3 double bonds and/or triple bonds and having 2–14 carbon atoms (which may be substituted with at least one substituent group selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein from 1 to 3 methylene groups may be replaced with carbonyl groups), or a straight-chain or branched chain saturated or unsaturated hydrocarbon group containing from 1 to 5 thioether, ether and/or amino bonds and having 1–14 carbon atoms (wherein hetero atoms are not bonded directly to A, and 1 to 3 methylene groups may be replaced with carbonyl groups);

R⁵ represents a hydrogen atom or an organic group (which may be substituted with at least one or more substituent groups selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, iodine, an amino group, a nitro group, a cyano group, an isothiocyanate group, a trifluoromethyl group and a methylenedioxy group); or R₅ is

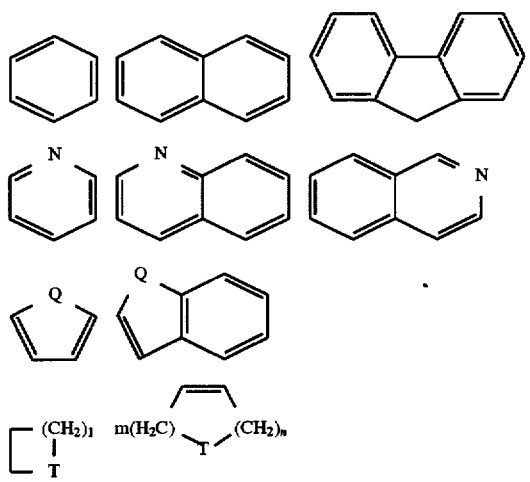

wherein

Q is N, O or S;

T is CH, N, S or O;

l is 0–5;

m and n are ≧0 m+n≦5;

R⁶ represents a hydrogen atom;

R⁷ represents a hydrogen atom, a hydroxy group, an alkoxy group having 1–5 carbon atoms, an alkanoyloxy group having 1–5 carbon atoms, or R⁶ and R⁷ together represent —O—, —CH₂— or —S—;

R⁸ represents a hydrogen atom, an alkyl group having 1–5 carbon atoms, or an alkanoyl group having 1–5 carbon atoms. The general formula (V) includes the (+) form, (−) form and (±) form of compounds.

Preferred compounds of Formula V are those wherein:

R¹ is an alkyl group having 1–5 carbon atoms, a cycloalkylmethyl group having 4–7 carbon atoms, a cycloalkenylmethyl group having 5–7 carbon atoms, a phenylalkyl group having 7–13 carbon atoms, an alkenyl group having 4–7 carbon atoms, an allyl group, a furan-2-yl-alkyl group having 1–5 carbon atoms or a thiophen-2-yl-alkyl group having 1–5 carbon atoms, while particularly preferred compounds are those wherein R¹ is methyl, ethyl, cyclopropylmethyl, cyclobutylmethyl, cyclopentylmethyl, cyclopentenylmethyl, cyclohexenylmethyl, benzyl, phenethyl, trans-2-butenyl, 2-methyl-2-butenyl, allyl, furan-2-yl-methyl or thiophen-2-yl-methyl groups;

R² is hydrogen, hydroxy, nitro, acetoxy, methoxy, methyl, ethyl, propyl, amino, dimethylamino, acetylamino or benzoylamino groups, while particularly preferred compounds are those wherein R² is hydrogen, hydroxy, nitro, acetoxy, methyl or dimethylamino groups;

R³ is hydrogen, hydroxy, acetoxy or methoxy;

A is —NR⁴C(=O)—, —NR⁴C(=S)—, —NR⁴C(=O)O—, —NR⁴C(=O)NR⁴—, —NR⁴C(=S)NR⁴—, —NR⁴C(=O)S—, —OC(=O)—, —OC(=O)O—, —SC(=O)—, —NR⁴—, —O—, —NR⁴SO₂— or —OSO₂—, while particularly preferred compounds are those wherein R³ is —NR⁴C(=O)—, —NR⁴C(=S)—, —NR⁴C(=O)O—, —NR⁴C(=O)NR⁴—, —NR⁴C(=S)NR⁴— or —NR⁴SO₂—;

R⁴ is hydrogen, a straight-chain or branched alkyl group having 1–5 carbon atoms or a phenyl group, while particularly particularly preferred compounds are those wherein R⁴ is a straight-chain or branched alkyl group having 1–5 carbon atoms, particularly methyl, ethyl, propyl, isopropyl, butyl and isobutyl groups; or R⁴ is Formula V-1

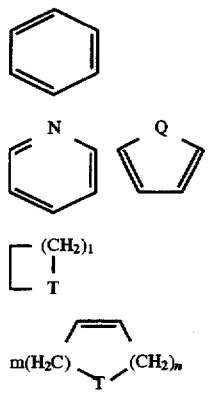

wherein
Q is N, O or S;
T is CH, N, S or O;
m and n are ≧0 and
m+n≦5;

B is —(CH₂)ₙ-(n=0–6), —(CH₂)ₙ—C(=O)-(n=1–4), —CH=CH—(CH₂)ₙ-(n=0–4), —C≡C—(CH₂)ₙ-(n=0–4), —CH₂—O—, —CH₂—S—, —CH₂—O—(CH₂)₂—O—(CH₂)₂—, —CH₂—O—CH₂—NH—CH₂—O—CH₂— or —CH₂—O—CH₂—S—CH₂—O—CH₂—, while particularly preferred compounds are those wherein B is —(CH₂)ₙ-(n=0–6), —CH=CH(CH₂)ₙ-(n=0–4), —C≡C—(CH₂)ₙ-(n=0–4), —CH₂—O— or —CH₂—S—;

R⁵ is hydrogen or an organic group having the basic skeleton indicated in (Formula V-1) (which may be substituted with at least one or more substituent groups selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, an amino group, a nitro group, a cyano group, an isothiocyanate group and a trifluoromethyl group), while particularly preferred compounds are those wherein R⁵ is hydrogen, phenyl, 3,4-dichlorophenyl, 4-chlorophenyl, 3-chlorophenyl, 3,4-difluorophenyl, 4-fluorophenyl, 3-fluorophenyl, 2-fluorophenyl, 4bromophonyl, 3-bromophenyl, 2-bromophenyl, 4-nitrophenyl, 3-nitrophenyl, 2-nitrophenyl, 4-trifluoromethylphenyl, 3-trifluoromethylphenyl, 2-trifluoromethylphenyl, 4-methylphenyl, 3-methylphenyl, 2-methylphenyl, 4-methoxyphenyl, 3-methoxyphenyl, 2-mothoxy, 3-furanyl, 2-furanyl, 3-thienyl, 2-thienyl, cyclopentyl or cyclohexyl groups.

Examples of preferred compounds include:

17-cyclopropylmethyl-4,5α-epoxy-3,14β-dihydroxy-6β-(N-methyl-3-phenylpropionamido)morphinan;
17-cyclopropylmethyl-4,5α-epoxy-3,14β-dihydroxy-6β-(N-methyl-trans-3-(3-furyl)acrylamido)morphinan;
17-cyclopropylmethyl-4,5α-epoxy-3,14β-dihydroxy-6β-(N-methyl-trans-3-cyclohexylacrylamido)morphinan;
17-cyclopropylmethyl-4,5α-epoxy-3,14β-dihydroxy-6β-(N-methyl-trans-3-(4-trifluoromethylphenyl)acrylamido)morphinan;
17-cyclopropylmethyl-4,5α-epoxy-3,14β-dihydroxy-6α-(N-methyl-trans-3-(3-thiophenyl)acrylamido)morphinan;
17-cyclopropylmethyl-4,5α-epoxy-3,14β-dihydroxy-6β-(N-methyl-trans-3-phenylacrylamido)morphinan;
17-cyclopropylmethyl-4,5α-epoxy-3,14β-dihydroxy-6β-(N-methyl-trans-2-hexenamido)morphinan; and
17-cyclopropylmethyl-4,5α-epoxy-3,14β-dihydroxy-6β-(N-methylphenylpropiolamido)morphinan.

DETAILED DESCRIPTION OF THE INVENTION

In a composition aspect, the kappa agonist compounds of the present invention for use of their anti-pruritic activity are formulated into parenteral, local and topical formulations.

The compositions are formulated as injectables, as oral and rectal formulations for systemic administration, and for local and topical administration as creams, aqueous or non-aqueous suspension, lotions, emulsions, suspensions or emulsions containing micronized particles, gels, foams aerosols, solids and other suitable vehicles for application to the skin, eyes, lips and mucosa, as suppositories or cream for vaginal administration, and as combinations with bandages, patches, bioadhesives and dressings.

In a method aspect the present invention provides method to treat or prevent pruritus by applying an amount of a compound or composition to a mammal to ameliorate or eliminate pruritus. Thus, the method of the present invention comprises a method of treating pruritus internally or externally present in the mammalian body including: irritation associated with inflammation following local infection, blisters, boils, or acute skin injuries, such as abrasions, burns, superficial cuts, surgical incisions, toothaches, contusions, irritations, inflammatory skin conditions, including but not limited to poison ivy, and allergic rashes and dermatitis and any condition that yields a pruritic state or condition.

FORMULATIONS OF THE PRESENT INVENTION

Effective concentrations of one or more of the compounds of the present invention or pharmaceutically acceptable derivatives thereof are mixed with a suitable pharmaceutical carrier or vehicle for systemic, topical or local administration. Compounds are included in an amount effective for reducing the pruritic state or for which treatment is contemplated. The concentration of active compound in the composition will depend on absorption, inactivation, excretion rates of the active compound, the dosage schedule, and amount administered as well as other factors known to those of skill in the art. For topical and local administration, the dosages are higher, typically at least about 5 to 10 fold, than the amount delivered when administered systemically orally.

The dosage of the compound of Formulas I, II Ia, IIb, III, IV and V for antipruritic purposes is from about 0.001 to about 20 mg/kg body weight of the patient. The compounds of Formulas I, II, Ia, IIb, III, IV and V are conveniently prepared in 5, 10, 25, 50, 75, 100 and 200 mg dosage units for administration for 1 to 4 times a day. Preferred unit dosages are from 0.05 to 10 mg/kg body weight of the patient.

The compounds are administered orally, parenterally, rectally and topically.

Pharmaceutical carriers or vehicles suitable for administration of the compounds and for the methods provided herein include any such carriers known to those skilled in the art to be suitable for the particular mode of administration. In addition, the compounds may be formulated as the sole pharmaceutically active ingredient in the composition or may be combined with other active ingredients.

a) Systemic Formulations

The formulations of the present invention are provided for administration to humans and animals in unit dosage forms, such as tablets, capsules, pills, powders, granules, sterile parenteral solutions or suspensions, and oral solutions or suspensions, and oil-water emulsions containing suitable quantities of a compound of Formulas I, II, IIa, IIb, III, IV and V or pharmacologically acceptable salts thereof.

Pharmaceutical dosage unit forms are prepared to provide from about 0.05 mg to about 500 mg and preferably from about 1.0 to about 200 mg of the essential active ingredient or a combination of essential ingredients per dosage unit form.

Oral pharmaceutical dosage forms are either solid or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Pharmaceutically acceptable carriers utilized in tablets are binders, lubricants, diluents, disintegrating agents, coloring agents, flavoring agents, and wetting agents. Enteric-coated tablets, due to their enteric-coating, resist the action of stomach acid and dissolve or disintegrate in the neutral or alkaline intestines. Sugar-coated tablets are compressed tablets to which different layers of pharmaceutically acceptable substances have been applied. Film-coated tablets are compressed tablets which have been coated with a water soluble polymer. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Examples of binders include glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Disintegrating agents include corn starch, potato starch, bentonite, methylcellulose, agar and carboxymethylcellulose. Coloring agents include, for example, any of the approved certified water soluble FD and C dyes, mixtures thereof, and water insoluble FD and C dyes suspended on alumia hydrate. Sweetening agents include sucrose, lactose, mannitol and artificial sweetening agents such as sodium cyclamate and saccharin, and any number of spray dried flavors. Flavoring agents include natural flavors extracted from plants such as fruits and synthetic blends of compounds which produce a pleasant sensation. Wetting agents include propylene glycol monostearate, sorbitan monooleate, diethylene glycol monolaurate and polyoxyethylene laural ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

Parenteral administration of the formulations of the present invention includes intravenous, subcutaneous and intramuscular administrations.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (Tween 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule or a syringe with a needle.

All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Pharmaceutical dosage forms for rectal administration are rectal suppositories, capsules and tablets for systemic effect.

Rectal suppositories are used herein mean solid bodies for insertion into the rectum which melt or soften at body temperature releasing one or more pharmacologically or therapeutically active ingredients.

Pharmaceutically acceptable substances utilized in rectal suppositories are bases or vehicles and agents to raise the melting point.

Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

The pharmaceutically therapeutically active compounds of Formulas I, II, Ia, IIb, III, IV and V are administered orally, parenterally or rectally in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses which are not segregated in packaging.

Compounds of the present invention in formulations may be included with other active compounds to obtain desired combinations of properties. Other active compounds with known pharmacological properties include analgesics such as aspirin, phenacetin acetaminophen, propoxyphene, pentazocine, codeine, meperidine, oxycodone, mefenamic acid, and ibuprofen; muscle relaxants such as methocarbamol, orphenadrine, carisoprodol, meprobamate, chlorphenesin carbamate, diazepam, chlordiazepoxide and chlorzoxazone; analeptics such as caffeine, methylphenidate and pentylenetetrazol; corticosteroids such as methylprednisolone, prednisone, prednisolone and dexamethasone; antihistamines such as chlorpheniramine, cyproheptadine, promethazine and pyrilamine.

b) Local and Topical Formulations

Typically a therapeutically effective dosage is formulated to contain a concentration of at least about 0.1% w/w up to about 50% w/w or more, preferably more than 1% w/w of the active compound to the treated tissue. The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the hyperalgesic or other condition and may be empirically determined.

Compounds are typically included at concentrations 0.001% w/w or greater than 1% w/w up to 50% w/w or higher. The concentration is generally greater than the concentration for systemic administration of the compound.

Preferable concentrations are in the range of 0.01% w/w to about 25% w/w, more preferably 1% w/w to 25% w/w, yet more preferably greater than about 1% w/w to about 10% w/w, and most preferably greater than 1% w/w up to about 5% w/w. Aqueous suspensions and formulations contain 1% w/w or more.

The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, or any other formulations suitable for topical or local administration.

The route of administration herein is topical or local administration, and compositions are formulated in a manner suitable for each route of administration. Preferred modes of administration include topical application to the skin, eyes or mucosa, and local application to the joints, such as by intra-articular injection. Thus, typical vehicles are those suitable for pharmaceutical or cosmetic application to body surfaces or for local injection.

Pharmaceutical and cosmetic carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients. The active compound is included in the carrier in an amount sufficient to exert a therapeutically useful effect in the absence of serious toxic effects on the treated individual. The effective concentration may be determined empirically by testing the compounds using in vitro and in vivo systems, including the animal models described herein.

For topical administration, the compounds may be formulated in compositions in the form of gels, creams, lotions, solids, solutions or suspensions, or aerosols. Compositions for treating human skin are formulated for topical application with an antihyperalgesic effective amount of one or more of the compounds selected as described herein, in an effective concentration range [by weight], between about 0.1% and 80%, preferably 0.1 to 50%, more preferably greater than about 1% up to about 50% or more in a cream, ointment, lotion, gel, solution or solid base or vehicle known in the art to be non-toxic and dermatologically acceptable or suitable for application to the mucosa. Aqueous suspensions are preferably formulated at concentrations greater than about 1% w/w, more preferably 2% w/w.

To formulate a composition, the weight fraction of compound is dissolved, suspended, dispersed or otherwise mixed in a selected vehicle at an effective concentration such that the hyperalgesic condition is relieved or ameliorated. Generally, emollient or lubricating vehicles that help hydrate the skin are more preferred than volatile vehicles, such as ethanol, that dry the skin. Examples of suitable bases or vehicles for preparing compositions for use with human skin are petrolatum, petrolatum plus volatile silicones, lanolin, cold cream [USP], and hydrophilic ointment [USP].

The choice of an acceptable vehicle is largely determined by the mode of application and tissue to be treated. Suitable pharmaceutically and dermatologically acceptable vehicles for topical application include those suited for use include lotions, creams, solutions, gels, tapes and the like. Generally, the vehicle is either organic in nature or an aqueous emulsion and capable of having the selected compound or compounds, which may be micronized, dispersed, suspended or dissolved therein. The vehicle may include pharmaceutically-acceptable emollients, skin penetration enhancers, coloring agents, fragrances, emulsifiers, thickening agents, and solvents.

For local internal administration, such as intra-articular administration, the compounds are preferably formulated as a suspension in an aqueous-based medium, such as isotonically buffered saline or are combined with a biocompatible support or bioadhesive intended for internal administration.

Lotions

The lotions contain an effective concentration of one or more of the compounds. The effective concatenation is preferably effective to deliver an anti-hyperalgesic amount, typically at a concentration of between about 0.1–50% w/w or more of one or more of the compounds provided herein. The lotions also contain from 1% to 50% w/w, preferably from 3% to 15% w/w of an emollient and the balance water, a suitable buffer, a $C_2$ or $C_3$ alcohol, or a mixture of water of the buffer and the alcohol. Any emollients known to those of skill in the art as suitable for application to human skin may be used. These include, but are not limited to, the following:

(a) Hydrocarbon oils and waxed, including mineral oil, petrolatum, paraffin, ceresin, ozokerite, microcrystalline wax, polyethylene, and perhydrosqualene.

(b) Silicone oils, including dimethylpolysiloxanes, methylphenylpolysiloxanes, water-soluble and alcohol-soluble silicone-glycol copolymers.

(c) Triglyceride fats and oils, including those derived from vegetable, animal and marine sources. Examples include, but are not limited to, castor oil, safflower oil, cotton seed oil, corn oil, olive oil, cod liver oil, almond oil, avocado oil, palm oil, sesame oil and soybean oil.

(d) Acetoglyceride esters, such as acetylated monoglycerides.

(e) Ethoxylated glycerides, such as ethoxylated glyceryl monostearate.

(f) Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, isopropyl myristate, decyl oleate, isodecyl oleate, hexadecyl stearate, decyl stearate, isopropyl isostearate diisopropyl adipate, diisohexyl adipate, dihexyldecyl adipate, diisopropyl sebacate, lauryl lactate, myristyl lactate, and cetyl lactate.

(g) Alkenyl esters of fatty acids having 10 to 20 carbon atoms. Examples thereof include, but are not limited to, oleyl myristate, oleyl stearate, and oleyl oleate.

(h) Fatty acids having 9 to 22 carbon atoms. Suitable examples include, but are not limited to pelargonic, lauric, myristic, palmitic, stearic, isostearic, hydroxystearic, oleic, linoleic, ricinoleic, arachidonic, behenic, and erucic acids.

(i) Fatty alcohols having 10 to 20 carbon atoms, such as but not limited to, lauryl, myristyl, cetyl, hexadecyl, stearyl, isostearyl, hydroxystearyl, oleyl, ricinoleyl, behenyl, erucyl, and 2-octyl dodecyl alcohols.

(j) Fatty alcohol ethers, including, but not limited to, ethoxylated fatty alcohols of 10 to 20 carbon atoms, such as, but are not limited to, the lauryl cetyl, stearyl, isostearyl, oleyl, and cholesterol alcohols having attached thereto from 1 to 50 ethylene oxide groups or 1 to 50 propylene oxide groups or mixtures thereof.

(k) Ether-esters, such as fatty acid esters of ethoxylated fatty alcohols.

(l) Lanolin and derivatives, including but not limited to, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases.

(m) Polyhydric alcohols and polyether derivatives, including, but not limited to, propylene glycol, dipropylene glycol, polypropylene glycol [M.W. 2000–4000], polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol [M.W. 200–6000], methoxy polyethylene glycols 350, 550, 750, 2000, 5000, poly)ethylene oxide) homopolymers [M.W. 100,000–5,000,000], polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}$–$C_{18}$ vicinal glycol and polyoxypropylene derivatives of trimethylolpropane.

(n) Polyhydric alcohol esters, including, but not limited to, ethylene glycol mono- and di-fatty acid esters, diethylene glycol mono- and di-fatty acid esters, polyethylene glycol [M.W. 200–6000], mono- and di-fatty esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

(o) Wax esters, including, but not limited to, beeswax, spermaceti, myristyl myristate, and stearyl stearate and beeswax derivatives, including, but not limited to, polyoxyethylene sorbitol beeswax, which are reaction products of beeswax with ethoxylated sorbitol of varying ethylene oxide content that form a mixture of ether-esters.

(p) Vegetable waxes, including, but not limited to, carnauba and candelilla waxes.

(q) Phospholipids, such as lecithin and derivatives.

(r) Sterols, including, but not limited to, cholesterol and cholesterol fatty acid esters.

(s) Amides, such as fatty acid amides, ethoxylated fatty acid amides, and solid fatty acid alkanolamides.

The lotions further preferably contain from 1% w/w to 10% w/w, more preferably from 2% w/w to 5% w/w, of an emulsifier. The emulsifiers can be nonionic, anionic or cationic. Examples of satisfactory nonionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxides mono- and di-fatty acid esters of ethylene glycol wherein the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include, but are not limited to, the fatty acid soaps, e.g. sodium, potassium and triethanolamine soaps, wherein the fatty acid moiety contains from 10 to 20 carbon atoms. Other suitable anionic emulsifiers include, but are not limited to, the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Among satisfactory cationic emulsifiers are quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably, the compound, is dissolved, suspended or otherwise uniformly dispersed in the mixture.

Other conventional components of such lotions may be included. One such additive is a thickening agent at a level from 1% to 10% w/w of the composition. Examples of suitable thickening agents include, but are not limited to: cross-linked carboxypolymethylene polymers, ethyl cellulose, polyethylene glycols, gum, tragacanth, gum kharaya, xanthan gums and bentonite, hydroxyethyl cellulose, and hydroxypropyl cellulose.

Creams

The creams are formulated to contain concentration effective to deliver an antipruritically effective amount of the compound to the treated tissue, typically at between about 0.1%, preferably at greater than 1% up to and greater than 50%, preferably between about 3% and 50%, more preferably between about 5% and 15% of one or more of the compounds provided herein. The creams also contain from 5% to 50%, preferably from 10% to 25%, of an emollient and the remainder is water or other suitable non-toxic carrier, such as an isotonic buffer. The emollients, as described above for the lotions, can also be used in the cream compositions. The cream may also contain a suitable emulsifier, as described above. The emulsifier is included in the composition at a level from 3% to 50%, preferably from 5% to 20%.

Solutions and suspensions for topical and local administration

The solutions are formulated to contain an amount of one or more compounds effective to deliver an anti-pruritic amount, typically at a concentration of between about 0.1–50% w/w, preferably at least more than 1% w/w, more preferably more than 2% w/w of one or more of the compounds provided herein. The balance is water, a suitable organic solvent or other suitable solvent or buffer. Suitable organic materials useful as the solvent or a part of a solvent system are as follows: propylene glycol, polyethylene glycol [M.W. 200–600], polypropylene glycol [M.W. 425–2025], glycerine, sorbitol esters, 1,2,6-hexanetriol, ethanol, isopropanol, diethyl tartrate, butanediol and mixtures thereof. Such solvent systems can also contain water.

Solutions or suspensions used for local application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agnets, such as ethylenediaminetetraacetic acid [EDTA]; buffers, such as acetates, citrates and phosphates; and agents for the adjustment of tonicity such as sodium chloride or dextrose. Liquid preparations can be enclosed in ampoules, disposable syringes or multiple dose vials made of glass, plastic or other suitable material. Suitable carriers may include physiological saline or phosphate buffered saline [PBS], and the suspensions and solutions may contain thickening and solubilizing agents, such as glucose, polyethylene glycol, and polypropylene glycol and mixtures thereof. Liposomal suspensions, may also be suitable as pharmaceutically acceptable carriers. These may be prepared according to methods known to those skilled in the art.

These compositions that are formulated as solutions or suspensions may be applied to the skin, or may be formulated as an aerosol or foam and applied to the skin as a spray-on. The aerosol compositions typically contain from 25% to 80% w/w, preferably from 30% to 50% w/w, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used as understood in the art in a quantity and under a pressure suitable to expel the contents of the container.

Suitably prepared solutions and suspension may also be topically applied to the eyes and mucosa. Solutions, particularly those intended for opthalmic use, may be formulated as 0.01%–10% w/w isotonic solutions, pH about 5–7, with appropriate salts, and preferably containing one or more of the compounds herein at a concentration of about 0.1% w/w preferably greater than 1% w/w, up to 50% w/w or more. Suitable opthalmic solutions are known [see, e.g. U.S. Pat. No. 5,116,868, which describes typical compositions of opthalmic irrigation solutions and solutions for topical application]. Such solutions, which have a pH adjusted to about 7.4, contain, for example, 90–100 mM sodium chloride, 4–6 mM dibasic potassium phosphate, 4–6 mM dibasic sodium phosphate, 8–12 mM sodium citrate, 0.5–1.5 mM magnesium chloride, 1.5–2.5 mM calcium chloride, 15–25 mM sodium acetate, 10–20 mM D.L.-sodium β-hydroxybutyrate and 5–5.5 mM glucose.

The active compounds of the present invention can also be mixed with other active materials, that do not impair the desired action, or with materials that supplement the desired action, including viscoelastic materials, such as hyaluronic acid, which is sold under the trademark HEALON [solution of a high molecular weight (MW of about 3 million) fraction of sodium hyaluronate; manufactured by Pharmacia, Inc. see, e.g., U.S. Pat. Nos. 5,292,362, 5,282,851, 5,273,056, 5,229,127, 4,517,295 and 4,328,803], VISCOAT [fluorine-containing (meth) acrylates, such as, 1H, 2H, 2H-heptadecafluorodecylmethacrylate; see, e.g., U.S. Pat. Nos. 5,278,126, 5,273,751 and 5,214,080; commercially available from Alcon Surgical, Inc.], ORCOLON [see, e.g., U.S. Pat. No. 5,273,056; commercially available from Optical Radiation Corporation], methylcellulose, methyl hyaluronate, polyacrylamide and polymethacrylamide [see, e.g., U.S. Pat. No. 5,273,751]. The viscoelastic materials are present generally in amounts ranging from about 0.5 to 5.0% w/w, preferably 1 to 3% w/w of the conjugate material and serve to coat and protect the treated tissues. The compositions may also include a dye, such as methylene blue or other inert dye, so that the composition can be seen when injected into the eye or contacted with the surgical site during surgery.

Gels

Gel compositions can be formulated by simply admixing a suitable thickening agent to the previously described solution or suspension composition. Examples of suitable thickening agents have been previously described with respect to the lotions.

The gelled compositions contain an effective amount of one or more of an antipruritic amount, typically at a concentration of between about 0.1–50% w/w or more of one or more of the compounds provided therein; from 5% to 75% w/w, preferably from 10% to 50% w/w, of an organic solvent as previously described; from 0.5% to 20% w/w, preferably from 1% to 10% w/w of the thickening agent; the balance being water or other aqueous carrier.

Solids

Compositions of solid forms may be formulated as stick-type compositions intended for application to the lips or other parts of the body. Such compositions contain an effective amount of one or more of the compounds provided therein. The amount is typically an amount effective to deliver an anti-pruritic amount, typically at a concentration of between about 0.1–50% w/w or more of one or more of the compounds provided herein. The solids also contain from about 40% to 98% w/w, preferably from about 50% to 905 w/w, of the previously described emollients. This composition can further contain from 1% to 20% w/w, preferably from 5% to 15% w/w, of a suitable thickening agent, and, if desired or needed, emulsifiers and water or buffers. Thickening agents previously described with respect to lotions are suitably employed in the composition in solid form.

Other ingredients such as preservatives, including methylparaben or ethyl-paraben, perfumes, dyes or the like, that are known in the art to provide desirable stability, fragrance or color, or other desirable properties, such as shielding from actinic rays from the sun, to compositions for application to the skin may also be employed in a composition for such topical application.

Combinations and kits

The compounds and compositions containing the compounds may also be coated on bandages, mixed with bioadhesives or included in dressings. Thus, combinations of bandages, bioadhesives, dressings and other such materials and the compositions formulated as described herein are provided. Kits containing these combinations, which may also include compositions containing the above listed agents, are also provided.

Articles of manufacture

The compounds and compositions provided herein may be packaged as articles of manufacture containing packaging material, one or more of the compounds provided herein, which is effective for ameliorating pruritus, within the packaging material, and a label that indicates that the compound, N-oxide, acid, salt or other derivative thereof is used for treating pruritic conditions.

Methods of treatment

Compositions for use with human skin preferably may be applied at least once per day, or if necessary, to achieve the desired result, more often, to the areas of the skin for which treatment is sought. It is understood that the precise treatment regimen depends upon the individual treated and may be ascertained empirically depending upon the formulation, and particularly, the age of the treated individual. Any regimen is acceptable as long as the desired anti-pruritic effects are achieved without substantial deleterious or sustained undesirable side effects.

The methods for treating human skin are practiced by applying to the skin, preferably at least daily, a composition suitable for human skin treatment or treatment of mucosal membranes and other body surface tissues, including the vagina, rectum, mouth, eyes and other such tissues. The compositions may be injected into joints or other inflamed areas.

Compositions may be combined with bandages, bioadhesives and other dressings and applied to the body in combination therewith.

The following examples are included for illustrative purposes only and are not intended to limit the scope of the invention.

EXAMPLE A

Capsules

| Active Compound | 2.5 gm |
|---|---|
| Corn starch | 23.0 gm |
| Lactose | 145.0 gm |
| Talc | 15.0 gm |
| Magnesium stearate | 3.0 gm |

The ingredients were mixed and were encapsulated using techniques practiced in the art.

EXAMPLE B

Tablet

| Active Compound | 150 gm |
|---|---|
| Lactose | 125 gm |
| Corn starch | 50 gm |
| Magnesium stearate | 2.0 gm |
| Liquid Petrolatum | 2.0 gm |

The ingredients were mixed, then put through U.S. Standard Screens to produce fine granules. The granules were compressed into tablets, each tablet containing about 150 mg of an active compound of the present invention.

EXAMPLE C

Syrup

| Active Compound | 25 gm |
|---|---|
| Lemon Oil | 2 ml |
| Sucrose | 650 gm |
| Citric Acid | 4 gm |
| Benzoic Acid | 3 gm |
| Tragacanth | 16 gm |
| Deionized water q.s. 1000 ml | |

The ingredients, without the active compound, are dispersed in water to make about 800 to 900 ml of solution. The active compound is then added and the solution is stirred into a syrup. Water is then added to make 1000 ml of the syrup.

EXAMPLE D

Parenteral Solution

| Active Compound | 30 gm |
|---|---|
| Methylparaben | 3 gm |
| Propylparaben | 1 gm |
| Lidocaine | 5 gm |
| Deionized water q.s. 1000 ml | |

The ingredients are dissolved in water to provide a solution followed by sterilization by filtration.

EXAMPLE E

Rectal Suppository

| Active Compound | 80 gm |
|---|---|
| Propylene glycol | 95 gm |
| Polyethylene glycol 4000 | 1800 gm |

The active compound is added to the propylene glycol and milled until a finely divided uniform mixture is formed. The polyethylene glycol 4000 is melted and the propylene glycol dispersion is added with stirring to obtain a suspension. The suspension is poured into molds, allowed to solidify and removed from the molds for packaging.

EXAMPLE F

Water-washable ointment

| Active Compound | 1.4% w/w |
|---|---|
| Lanolin alcohol | 0.15 w/w |
| Emulsifying wax NF | 7.5% w/w |
| PEG-20 glycerides | 5.0% w/w |
| Petrolatum | 86.0% w/w |

The ingredients are melted together and mixed well until the resulting ointment congeals.

EXAMPLE G

Oil-in-water cream

| Active Compound | 10.0% w/w |
|---|---|
| Benzyl alcohol | 4.0% w/w |
| Propylene glycol | 10.0% w/w |
| Polyethylene glycol 400 | 10.0% w/w |
| Petrolatum | 20.0% w/w |
| Stearyl alcohol | 10.0% w/w |
| Poloxamer | 10.0% w/w |
| Water q.s. | 100 |
| Buffer to pH | 7.0% w/w |

In preparing the oil-in-water cream, water, propylene glycol and polyethylene glycol 400 are heated to about 70° to 80° C., followed by adding a mixture of petrolatum, stearyl alcohol and poloxamer and the mixture is stirred until homogeneous. The active compound in benzyl alcohol is added and the mixture is homogenized. The pH is then adjusted with a buffer to about 7.0.

EXAMPLE H

Aqueous gel

| Active Compound | 10.0% w/w |
|---|---|
| Benzyl alcohol | 4.0% w/w |
| Hydroxyethyl cellulose | 3.0% w/w |
| Water q.s. | 100 |
| Buffer to pH | 7.0% w/w |

The aqueous gel is prepared by mixing the active compound, benzyl alcohol and adding the mixture to buffered water. Hydroxyethyl cellulose is then added with stirring until the mixture gels.

TESTING OF THE COMPOSITIONS FOR ANTIPRURITIC ACTIVITY

Testing was performed in a mouse scratch model under blind conditions.

Groups of 8–10 male Swiss albino mice (Hilltop Lab Animals, Inc., Scottsdale, Pa.), weighing 2.5–2.6 g, were used in the testing. They were housed under controlled temperature of 23°–25° C. Food and water were freely available. Before the experiments, the mice were weighted, put into individual boxes and allowed to acclimate for 30 min.

Materials

Vehicle used to dissolve the test compounds: 20% w/w cremafor EL.

To induce scratching Compound 48/80 (Sigma, St. Louis, USA) was used which has been shown to produce an itch sensation in humans (Armstrong et al., J. of Physiol., 120: 326,1953).

The compounds to be tested for anti-pruritic activity were dissolved in the vehicle of 20% w/w cremafor EL.

Method

100 μl of the vehicle (3–5 doses, n=8–10) was injected s.c. into the back of the neck of mice 20 min. before challenging them with 100 μl of Compound 48/80 (2 mg/ml; 50 μg) injected s.c. into the back of the neck. One minute later the mice were observed for 30 min. and the number of hindleg scratching movements directed to the neck was counted.

The vehicle-injected mice scratched 79±16 times in the 30 min after the standard challenge with Compound 48/80.

To each mouse of a group of 8–10 mice previously subjected to the standard challenge various doses of the compounds, to be tested for anti-pruritic activity, were administered s.c. into the back of the neck. One minute later the mice were observed for 30 min and the number of hindleg scratching movements directed to the neck was counted.

For each group of 8–10 mice, the mean values for scratching were normalized to relative % antagonism of scratching and then plotted vs. dose of test compounds. Interval estimates of mean $A_{50}$ were determined by nonlinear regression analysis (Kaleida Graph) and mean % inhibition of scratching was calculated.

Representative results are shown in Table I.

TABLE I

| Compound | mg/kg s.c. | % Inhibition |
|---|---|---|
| | 2.5 | 30 |
| | 5.0 | 57 |
| | 10.0 | 75 |
| | 30.0 | 92 |

TABLE I-continued

| Compound | mg/kg s.c. | % Inhibition |
|---|---|---|
| | 2.5 | 24 |
| | 5.0 | 72 |
| | 10.0 | 85 |

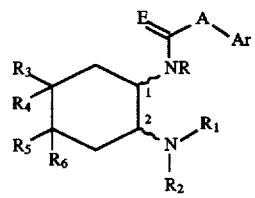

Other compounds tested have shown anti-pruritic, dose-responsive activity in the range of from about 15 to about 95% based on doses of from about 0.5 to 10.0 mg/kg, s.c.

It should be understood by those skilled in the art that, while the invention has been described and illustrated above in connection with certain specific embodiments, many variations and modifications may be employed without departing from the scope of the invention.

What is claimed is:

1. A method for the prevention or treatment of pruritus in a mammal in need of such prevention or treatment comprising administering to said mammal an effective anti-pruritic amount of a composition comprising a compound of formula I or a pharmaceutically acceptable salt thereof wherein the wavy line bond (~) between the nitrogen in the 2-position and the cyclohexyl ring carbon indicates the bond can be either cis- or trans with respect to each substituent on the cyclohexyl ring;

A is a single chemical bond (-), —(CH$_2$)$_q$, CH(CH$_3$)— or —X(CH$_2$)$_n$ where q is 1 to 4, n is 1–4 and x is O or S;

Ar is an aromatic, hetero-aromatic, bicyclic-aromatic, tricyclic-aromatic group or diphenyl methyl each of which may be unsubstituted or substituted with a member selected from the group consisting of H, halo, trifluoromethyl, nitro, $C_1$–$C_3$-alkoxy, hydroxy, azido, $C_1$–$C_3$-alkyl, methanesulfonyl, cyano, amino, $C_1$–$C_3$-alkoxycarbonyl, $C_1$–$C_3$-alkanoyloxy, and $C_1$–$C_3$-carboxacylamino of the formula —NHC(O)R$_7$ where R$_7$ is H, $C_1$–$C_2$-alkyl, and aromatic or hetero-aromatic group;

R$_1$ and R$_2$ are independently H, $C_1$–$C_3$-alkyl or allyl;

R₁ and R₂, taken together with the nitrogen to which they are bonded, complete a ring selected from the group consisting of azetidinyl, pyrrolidinyl, 3-hydroxypyrrolidinyl, 3-fluoropyrrolidinyl, morpholinyl, piperidinyl, and 3,4-dehydropiperidinyl;

R₃, R₄, R₅, R₆ are independently H, hydroxy, OR₈ or OC(=O)R₉;

R₅ and R₆ taken together may form the group —E—CH₂—CH₂—E—;

R₅ and R₆ taken together may form a ring

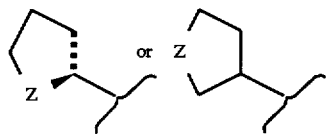

where

Z is selected from the group consisting of oxygen (—O—), NR₁₀, sulfur (—S—), sulfinyl (—S(O)—), and sulfonyl (—S(O)₂—);

E is N—OH, N—OC(O)CH₃, O, S, with the proviso that when E is bivalent sulfur or oxygen, R₅ and R₆ cannot both be hydrogen;

R₈ is C₁-C₃-alkyl;

R₉ is H or C₁-C₃-alkyl;

R₁₀ is H, or C₁-C₃-alkyl, in a pharmaceutically acceptable carrier.

2. A method of claim 1 wherein said compound is selected from the group consisting of:

(±)-N-[2-(N,N'-dimethylamino)cyclohexyl]-N-methyl-2-(4-trifluoromethylphenyl)acetamide;
(±)-N-[2-(N',N'-dimethylamino)cyclohexyl]-N-propyl-2-(3-methoxyphenyl)acetamide;
(±)-N-[2-(N',N'-dimethylamino)cyclohexyl]-N-methyl-2-(4-azidophenyl)acetamide;
(±)-N-[2-(N',N'-dimethylamino)cyclohexyl]-N-methyl-2-(3,4-dichlorophenyl)acetamide;
(±)-N-[2-(N',N'-dimethylamino)cyclohexyl]-N-methyl-2-(4-methoxyphenyl)acetamide;
(±)-N-[2-(N',N'dimethylamino)cyclohexyl]-N-methyl-2-(2-naphthyl)acetamide;
(±)-N-[2-(N-cyclopropyl-N-methylamino)cyclohexyl]-2-(4-azidophenyl)acetamide;
(±)-N-(2-(3-acetoxy-1-pyrrolidinyl)cyclohexyl]-N-methyl-2-(3,4-dichlorophenyl)acetamide;
(±)-N-[2-(N-pyrrolidinyl)cyclohexyl]-N-methyl-2-(3,4-dichlorophenyl)acetamide;
(±)-N-[2-(3-hydroxypyrrolidinyl)cyclohexyl]-N-methyl-2-(3,4-dichlorophenyl)acetamide;
(±)-N-[2-[N'-(3-hydroxy-1-azetidinyl]cyclohexyl]methyl-2-(3,4-dichlorophenyl)acetamide;
(±)-N-[2-(N',N'-diethylamino)cyclohexyl]-N-methyl-2-(3,4-dichlorophenyl)acetamide;
(±)-N-[2-(N'-pyrrolidinyl)cyclohexyl]-N-methyl-2-(3,4-dichlorophenyl)propionamide;
(±)-N-[2-(4-methyl-1-piperazinyl)cyclopentyl]-2-(3,4-dichlorophenyl)acetamide;
(±)-N-[2-(N,N-dimethylamino)cyclohexyl]-2-(3,4-dichlorophenyl)acetamide;
(±)-3,4-dichloro-N-methyl-N-[8-(1-pyrrolidinyl)-1,4-dioxaspiro[4.5]dec-7-yl]-benzeneacetamide;
(±)-3,4-dichloro-N-methyl-N-[7-(1-pyrrolidinyl)-1,4-dioxaspiro[4.5]dec-8-yl]-benzeneacetamide;
(±)-3,4-dichloro-N-methyl-N-[7-(1-pyrrolidinyl)-1,4-dioxaspiro[4.5]dec-6-yl]-benzeneacetamide;
(±)-4-bromo-N-methyl-N-[7-(1-pyrrolidinyl)-1,4-dioxaspiro[4.5]dec.8.yl]-benzeneacetamide;
(±)-3,fluoro-N-ethyl-N-[7-(1-azetidinyl)-1,4-dioxaspiro[4.5]dec-8-yl]benzeneacetamide;
(±)-3,4-dichloro-N-methyl-N-[7-(1-pyrrolidinyl)-1,4-dioxaspiro[4.4]-non-8-yl)benzeneacetamide;
(±)-3,4-dichloro-N-methyl-N-[7-(1-pyrrolidinyl)-1,4-dioxaspiro[4.6]-undec-8-yl]benzeneacetamide;
(±)-3,4-dichloro-N-methyl-N-[8-(1-pyrrolidinyl)-1,4-dioxaspiro[4.6]-undec-7-yl]benzeneacetamide;
(±)-3,4-dichloro-N-methyl-N-[9-(1-pyrrolidinyl)-1,4-dioxaspiro[4.6]-undec-8-yl]benzeneacetamide;
(±)-3,4-dichloro-N-[4-methoxy-2-(1-pyrrolidinyl)cyclohexyl]-N-methylbenzeneacetamide;
(±)-3,4-dichloro-N-[5-methoxy-2-(1-pyrrolidinyl)cyclohexyl]-N-methylbenzeneacetamide;
(±)-3,4-dichloro-N-methyl-N-[4-oxo-2-(1-pyrrolidinyl)cyclohexyl]-benzeneacetamide;
(±)-4-bromo-N-methyl-N-[2-(N',N'-dimethylamino)-4-oxocyclohexyl]benzeneacetamide;
(±)-N-[4-acetyloxy-2-(1-pyrrolidinyl)cyclohexyl]-3,4-dichloro-N-methylbenzeneacetamide;
(±)-N-[4-acetyloxy-2-aminocyclohexyl]-3,4-difluoro-N-methylbenzeneacetamide;
(±)-3,4-dichloro-N-[5-(hydroxyimino)-2-(1-pyrrolidinyl)cyclohexyl]-N-methylbenzeneacetamide;
(±)-3,4-dichloro-N-[4,4-dimethoxy-2-(1-pyrrolidinyl)cyclohexyl]-N-methylbenzeneacetamide which can also be named:
(±)-3,4-dichloro-N-methyl-N-[4-oxo-2-(1-pyrrolidinyl)cyclohexyl]benzeneacetamide, dimethyl ketal;
(±)-3,4-dichloro-N-[5,5-diethoxy-2-(1-pyrrolidinyl)cyclohexyl]-N-methylbenzeneacetamide;
(±)-(1α,2β)-3,4-dichloro-N-[4,4-dimethoxy-2-(1-pyrrolidinyl)cyclohexyl]-N-methylbenzeneacetamide;
(±)-4-trifluoromethyl-N-[4,4-dimethoxy-2-(1-pyrrolidinyl)cyclohexyl]-N-methylbenzeneacetamide;
(±)-3-trifluoromethyl-N-[4,4-diethoxy-2-(1-pyrrolidinyl)-cyclohexyl]-N-methylbenzeneacetamide;
(±)-3-hydroxy-4-methyl-N-[4,4-dimethoxy-2-(1-pyrrolidinyl)cyclohexyl]-N-methylbenzeneacetamide;
(±)-4-methanesulfonyl-N-[4,4-dimethoxy-2-(1-piperidinyl)-cyclohexyl]-N-methylbenzamide;
(±)-4-acetyloxy-N-[4,4-dimethoxy-2-(1-pyrrolidinyl)-cyclohexyl-N-methylbenzeneacetamide;
(±)-N-[4,4-bis(methylthio)-2-(1-pyrrolidinyl)cyclohexyl]-3,4-dichloro-N-methylbenzeneacetamide;
(±)-N-[5,5-bis(ethylthio)-2-(1-pyrrolidinyl)cyclohexyl]-3,4-di-chloro-N-methylbenzeneacetamide;
(±)-3,4-dichloro-N-[4-methylthio-2-(1-pyrrolidinyl)cyclohexyl]-N-methylbenzeneacetamide;
(±)-3,4-dichloro-N-[5-ethylthio-2-(1-pyrrolidinyl)cyclohexyl]-N-methylbenzeneacetamide;
(±)-3,4-dichloro-N-[6-methylthio-2-(1-pyrrolidinyl)cycloheptyl]-N-methylbenzeneacetamide;
(±)-3,4-dichloro-N-[4-mercapto-2-(1-pyrrolidinyl)cyclohexyl]-N-methylbenzeneacetamide;
[1R-(1α,2β,4β,5β)]-N-[4,5-dimethoxy-2-(1-pyrrolidinyl)cyclohexyl]-N-methyl-4-benzofuranacetamide;
[1S-(1α,2β,4β,5β)]-N-[4,5-dimethoxy-2-(1-pyrrolidinyl)cyclohexyl]-N-methyl-4-benzofuranacetamide;
[1R-(1α,2β,4α,5α)]-N-[4,5-dimethoxy-2-(1-pyrrolidinyl)cyclohexyl]-N-methyl-4-benzofuranacetamide;
[1S-(1α,2β,4α,5α)]-N-[4,5-dimethoxy-2-(1-pyrrolidinyl)cyclohexyl]-N-methyl-4-benzofuranacetamide;
[1R-(1α,2β,4β,5β)]-N-[4,5-dimethoxy-2-(1-pyrrolidinyl)cyclohexyl]-N-methylbenzo[b]thiophene-4-acetamide;

[1S-(1α,2β,4β,5β)]-N-[4,5-dimethoxy-2-(1-pyrrolidinyl)
cyclohexyl]-N-methylbenzo[b]thiophene-4-acetamide;
[1R-(1α,2β,4α,5α)]-N-[4,5-dimethoxy-2-(1-pyrrolidinyl)
cyclohexyl]-N-methylbenzo[b]thiophene-4-acetamide;
[1S-(1α,2β,4α,5α)]-N-[4,5-dimethoxy-2-(1-pyrrolidinyl)
cyclohexyl]-N-methylbenzo[b]thiophene-4-acetamide;
[1R-(1α,2β,4β,5β)]-N-[4,5-dimethoxy-2-(1-pyrrolidinyl)
cyclohexyl]-N-methyl-1-naphthaleneacetamide;
[1S-(1α,2β,4β,5β)]-N-[4,5-dimethoxy-2-(1-pyrrolidinyl)
cyclohexyl]-N-methyl-1-naphthaleneacetamide;
[1R-(1α,2β,4α,5α)]-N-[4,5-dimethoxy-2-(1-pyrrolidinyl)
cyclohexyl]-N-methyl-1-naphthaleneacetamide;
[1S-(1α,2β,4α,5α)]-N-[4,5-dimethoxy-2-(1-pyrrolidinyl)
cyclohexyl]-N-methyl-1-naphthaleneacetamide;
[1R-(1α,2β,4β,5β)]-3,4-dichloro-N-[4,5-dimethoxy-2-(1-
pyrrolidinyl)cyclohexyl]-N-methylbenzeneacetamide;
[1S-(1α,2β,4β,5β)]-3,4-dichloro-N-[4,5-dimethoxy-2-(1-
pyrrolidinyl)cyclohexyl]-N-methylbenzeneacetamide;
[1R-(1α,2β,4α,5α)]-3,4-dichloro-N-[4,5-dimethoxy-2-(1-
pyrrolidinyl)cyclohexyl]-N-methylbenzeneacetamide;
[1S-(1α,2β,4α,5α)]-3,4-dichloro-N-[4,5-dimethoxy-2-(1-
pyrrolidinyl)cyclohexyl]-N-methylbenzeneacetamide;
[1R-(1α,2β,4β,5β)]-N-[4,5-dimethoxy-2-(1-pyrrolidinyl)
cyclohexyl]-N-methyl-9H-fluorene-9-carboxamide;
[1S-(1α,2β,4β,5β)]-N-[4,5-dimethoxy-2-(1-pyrrolidinyl)
cyclohexyl]-N-methyl-9H-fluorene-9-carboxamide;
[1R-(1α,2β,4α,5α)]-N-[4,5-dimethoxy-2-(1-pyrrolidinyl)
cyclohexyl]-N-methyl-9H-fluorene-9-carboxamide;
[1S-(1α,2β,4α,5α)]-N-[4,5-dimethoxy-2-(1-pyrrolidinyl)
cyclohexyl]-N-methyl-9H-fluorene-9-carboxamide;
(±)-(1α,2β,4β)-N-methyl-N-[4-methoxy-2-(1-pyrrolidinyl)
cyclohexyl]-4-benzofuranacetamide;
(±)-(1α,2β,4α)-N-methyl-N-[4-methoxy-2-(1-pyrrolidinyl)
cyclohexyl]-4-benzofuranacetamide;
(±)-(1α,2β,5β)-N-methyl-N-[5-methoxy-2-(1-pyrrolidinyl)
cyclohexyl]-4-benzofuranacetamide;
(±)-(1α,2β,5α)-N-methyl-N-[5-methoxy-2-(1-pyrrolidinyl)
cyclohexyl]-4-benzofuranacetamide;
(±)-(1α,2β,4α)-N-[4-methoxy-2-(1-pyrrolidinyl)
cyclohexyl]-N-methyl-9H-fluorene-9-carboxamide;
(±)-(1α,2β,5β)-N-[5-methoxy-2-(1-pyrrolidinyl)
cyclohexyl]-N-methyl-9H-fluorene-9-carboxamide;
(±)-N-methyl-2-(1-naphthalenyloxy)-N-[2-(1-pyrrolidinyl)
cyclohexyl]acetamide;
(±)-N-methyl-2-(2-naphthalenyoxy)-N-[2-(1-pyrrolidinyl)
cyclohexyl]acetamide;
(±)-1,2-dihydro-N-methyl-N-[2-(1-pyrrolidinyl)cyclohexyl]
-1-acenaphthylenecarboxamide, (isomer I, mixture of
(1α, 2β) and (1β,2α) forms);
(±)-1,2-dihydro-N-methyl-N-[2-(1-pyrrolidinyl)cyclohexyl]
-1-acenaphthylenecarboxamide, (isomer II, mixture
of(1α, 2β) and (1β,2α) forms);
(±)-N-[4,5-dimethoxy-2-(1-pyrrolidinyl)cyclohexyl]-1,2-
dihydro-N-methyl-1-acenaphthylenecarboxamide
(isomer I, mixture of (1α,2β, 4β,5β) and (1β, 2α, 4α, 5α
forms);
(±)-N-[4,5-dimethoxy-2-(1-pyrrolidinyl)cyclohexyl]-1,2-
dihydro-N-methyl-1-acenaphthylenecarboxamide
(isomer II, mixture of (1α,2β, 4β, 5β) and (1β, 2α, 4α, 5α
forms);
(±)-1,2-dihydro-N-[4-methoxy-2-(1-pyrrolidinyl)
cyclohexyl]-N-methyl-1-acenaphthylenecarboxamide
(isomers I and II, mixtures of (1α, 2α, 4α) and (1α,2β,
4β) forms);
(±)-1,2-dihydro-N-[4-methoxy-2-(1-pyrrolidinyl)
cyclohexyl]-N-methyl-1-acenaphthylenecarboxamide
(isomers I and II, mixtures of (1β, 2α, 4α) and (1α,2β, 4β)
forms);
(±)-trans-N-methyl-N-[2-(1-pyrrolidinyl)cyclohexyl]-9H-
fluorene-9-carboxamide;
(±)-trans-1,3-dihydro-N-methyl-1-oxo-N-[2-(1pyrrolidinyl)
cyclohexyl]-4-isobenzofuranacetamide;
(±)-(1α,2β, 4β, 5β)-N-[4,5-dimethoxy-2-(1-pyrrolidinyl)
cyclohexyl]-1,3-dihydro-N-methyl-1-oxo-4-
isobenzofuranacetamide;
(±)-(5α,7α, 8β)-3,4-dichloro-N-methyl-N-[7-(1-
pyrrolidinyl)-1-oxaspiro[4.5]dec-8-benzeneacetamide;
(±)-(5α,7α, 8β)-bromo-N-methyl-N-[7-(1-pyrrolidinyl)-1-
oxaspiro[4.5]dec-8-yl]benzeneacetamide;
(±)-(5α,7α, 8β)-4-methoxy-N-methyl-N-[7-(1-pyrrolidinyl)
-1-oxaspiro[4.5]dec-8-yl]benzeneacetamide;
(±)-(5α,7α, 8β)-N-methyl-2-nitro-N-[7-(1-pyrrolidinyl)-1-
oxaspiro[4.5]dec-8-yl]benzeneacetamide;
(±)-(5α,7α, 8β)-N-methyl-3-nitro-N-[7-(1-pyrrolidinyl)-1-
oxaspiro[4.5]dec-8-yl]benzeneacetamide;
(±)-(5α,7α, 8β)-N-methyl-4-nitro-N-[7-(1-pyrrolidinyl)-1-
oxaspiro[4.5]dec-8-yl]benzeneacetamide;
(±)-(5α,7α, 8β)-N-methyl-N-[7-(1-pyrrolidinyl)-1-oxaspiro
[4.5]dec-8-yl]-3-(trifluoromethyl)benzeneacetamide;
(±)-(5α,6α, 7β)-3,4-dichloro-N-methyl-N-[7-(1-
pyrrolidinyl)-1-oxaspiro[4.5]dec-8-yl]benzeneacetamide;
(±)-(5α,7α, 8β)-3,4-dichloro-N-methyl-N-[7-(1-
pyrrolidinyl)-1-thiaspiro[4.5]dec-6-yl]benzeneacetamide;
(±)-(5α,7β, 8α)-3,4-dichloro-N-methyl-N-[8-(1-
pyrrolidinyl)-1-oxaspiro[4.5]dec-7-yl benzeneacetamide;
(±)-(5α,7α, 8β)-3,4-dichloro-1,N-dimethyl-[7-(1-
pyrrolidinyl)-1-azaspiro[4.5]dec-8yl benzeneacetamide;
(±)-(5α,7α, 8β)-4-bromo-N-methyl-N-[7-(1-pyrrolidinyl)-
1-azaspiro[4.5]dec-8-yl]benzamide;
(±)-(5α,7α, 8β)-3,4-dichloro-N-methyl-N-[7-(1-
pyrrolidinyl)-1-thiaspiro[4.5]dec-8-yl]benzamide;
(±)-(5α,7α, 8β)-3,4-dichloro-N-methyl-N-[7-(1-
pyrrolidinyl)-1-thiaspiro[4.5]dec-8-yl]benzeneacetamide;
(±)-(5α,7α, 8β)-3,4-dichloro-N-methyl-N-[7-(1-
pyrrolidinyl)-1-thiaspiro[4.5]dec-8-yl]benzeneacetamide;
(±)-(5α,7α, 8β)-3,4-dichloro-N-methyl-N-[7-(1-
pyrrolidinyl)-1-thiaspiro[4.5]dec-8-yl]benzeneacetamide,
1,1-dioxide;
(±)-(5α,7α, 8β)-N-methyl-N-[7-(1-pyrrolidinyl)-1-azaspiro
[4.5]dec-8-yl]4-trifluoromethylbenzeneacetamide;
(±)-(5α,7α, 8β)-N-methyl-N-[8-(1-pyrrolidinyl)-1-thiaspiro
[4.5]dec-7-yl]-3-trifluoromethylbenzeneacetamide;
[5R-(5α,7α,8β)]-N-Methyl-[7-(1-pyrrolidinyl)-1-oxaspiro
[4.5]dec-8-yl]-1H-indene-3-acetamide;
[5S-(5α,7α,8β)]-N-Methyl-[7-(1-pyrrolidinyl)-1-oxaspiro
[4.5]dec-8-yl]-1H-indene-3-acetamide;
[5R-(5α,7β,8α)]-N-Methyl-[7-(1-pyrrolidinyl)-1-oxaspiro
[4.5]dec-8-yl]-1H-indene-3-acetamide;
[5S-(5α,7β,8α)]-N-Methyl-[7-(1-pyrrolidinyl)-1-oxaspiro
[4.5]dec-8-yl]-1H-indene-3-acetamide;
[5R-(5α,7α,8β)]-N-Methyl-N-[7-(1-pyrrolidinyl)-1-
oxaspiro[4.5]dec-8-yl]-1H-indole-3-acetamide;
[5S-(5α,7α,8β)]-N-Methyl-N-[7-(1-pyrrolidinyl)-1-
oxaspiro[4.5]dec-8-yl]-1H-indole-3-acetamide;
[5R-(5α,7β,8α)]-N-Methyl-N-[7-(1-pyrrolidinyl)-1-
oxaspiro[4.5]dec-8-yl]-1H-indole-3-acetamide;
[5S-(5α,7β,8α)]-N-Methyl-N-[7-(1-pyrrolidinyl)-1-
oxaspiro[4.5]dec-8-yl]-1H-indole-3-acetamide;
[5R-(5α,7α,8β)]-N-Methyl-N-[7-(1-pyrrolidinyl)-1-
oxaspiro[4.5]dec-8-yl]-2-benzofuranacetamide;
[5S-(5α,7α,8β)]-N-Methyl-N-[7-(1-pyrrolidinyl)-1-
oxaspiro[4.5]dec-8-yl]-2-benzofuranacetamide;
[5R-(5α,7β,8α)]-N-Methyl-N-[7-(1-pyrrolidinyl)-1-
oxaspiro[4.5]dec-8-yl]-2-benzo[b]furanacetamide;
[5S-(5α,7β,8α)]-N-Methyl-N-[7-(1-pyrrolidinyl)-1-
oxaspiro[4.5]dec-8-yl]-2-benzo[b]furanacetamide;

[5R-(5α,7α,8β)]-N-Methyl-N-[7-(1-pyrrolidinyl)-1-oxaspiro[4.5]dec-8-yl]-3-benzo[b]furanacetamide;
[5S-(5α,7α,8β)]-N-Methyl-N-[7-(1-pyrrolidinyl)-1-oxaspiro[4.5]dec-8-yl]-3-benzo[b]furanacetamide;
[5R-(5α,7β,8α)]-N-Methyl-N-[7-(1-pyrrolidinyl)-1-oxaspiro[4.5]dec-8-yl]-3-benzo[b]furanacetamide;
[5S-(5α,7β,8α)]-N-Methyl-N-[7-(1-pyrrolidinyl)-1-oxaspiro[4.5]dec-8-yl]-3-benzo[b]furanacetamide;
[5R-(5α,7α,8β)]-N-Methyl-N-[7-(1-pyrrolidinyl)-1-oxaspiro[4.5]dec-8-yl]-4-benzo[b]furanacetamide;
[5S-(5α,7α,8β)]-N-Methyl-N-[7-(1-pyrrolidinyl)-1-oxaspiro[4.5]dec-8-yl]-4-benzo[b]furanacetamide;
[5R-(5α,7β,8α)]-N-Methyl-N-[7-(1-pyrrolidinyl)-1-oxaspiro[4.5]dec-8-yl]-4-benzo[b]furanacetamide;
[5S-(5α,7β,8α)]-N-Methyl-N-[7-(1-pyrrolidinyl)-1-oxaspiro[4.5]dec-8-yl]-4-benzo[b]furanacetamide;
[5R-(5α,7α,8β)]-N-Methyl-N-7-(1-pyrrolidinyl)-1-oxaspiro[4.5]dec-8-yl-4-benzo[b]thiophene-4-acetamide;
[5S-(5α,7α,8β)]-N-Methyl-N-7-(1-pyrrolidinyl)-1-oxaspiro[4.5]dec-8-yl-4-benzo[b]thiophene-4-acetamide;
[5R-(5α,7β,8α)]-N-Methyl-N-7-(1-pyrrolidinyl)-1-oxaspiro[4.5]dec-8-yl-4-benzo[b]thiophene-4-acetamide;
[5S-(5α,7β,8α)]-N-Methyl-N-7-(1-pyrrolidinyl)-1-oxaspiro[4.5]dec-8-yl-4-benzo[b]thiophene-4-acetamide;
(−)-(5α,7α,8β)]-N-Methyl-N-[7-(1-pyrrolidinyl)-1-oxaspiro[4.5]dec-8-yl]-4-benzo[b]furanacetamide;
(−)-(5α,7α,8β)]-N-7-(1-pyrrolidinyl)-1-oxaspiro[4.5]dec-8-yl-4-benzo[b]thiophene-4-acetamide;
(±)-(5α,6α,7β)-3,4-dichloro-N-methyl-N-[7-(1-pyrrolidinyl)-2-oxaspiro[4.5]dec-6-yl]benzeneacetamide;
(±)-(5α,6α,7β)-3,4-dichloro-N-methyl-N-[6-(1-pyrrolidinyl)-2-oxaspiro[4.5]dec-7-yl]benzeneacetamide, and
(±)-(5α,7α,8β)-3,4-dichloro-N-methyl-N-[8-(1-pyrrolidinyl)-2-oxaspiro[4.5]dec-7-yl]benzeneacetamide.

3. The method of claim 1 wherein said administration is topical administration.

4. The method of claim 1 wherein said administration is parenteral administration.

5. The method of claim 1 wherein said administration is oral administration.

6. The method of claim 1 wherein said administration is rectal administration.

7. The method of claim 2 wherein said administration is topical administration.

8. The method of claim 2 wherein said administration is parenteral administration.

9. The method of claim 2 wherein said administration is oral administration.

10. The method of claim 2 wherein said administration is rectal administration.

* * * * *